United States Patent [19]

Alizon et al.

[11] Patent Number: 5,580,739
[45] Date of Patent: Dec. 3, 1996

[54] PEPTIDES OF HUMAN IMMUNODEFICIENCY VIRUS TYPE 2 (HIV-2) AND IN VITRO DIAGNOSTIC METHODS AND KITS EMPLOYING THE PEPTIDES FOR THE DETECTION OF HIV-2

[75] Inventors: Marc Alizon, Paris; Luc Montagnier, Le Plessis Robinson; Denise Geutard, Paris, all of France; Francois Clavel, Rockville, Md.; Pierre Sonigo; Mireille Guyader, both of Paris, France

[73] Assignee: Institut Pasteur, Paris, France

[21] Appl. No.: 214,221

[22] Filed: Mar. 17, 1994

Related U.S. Application Data

[62] Division of Ser. No. 810,908, Dec. 20, 1991, abandoned, which is a division of Ser. No. 752,368, Sep. 3, 1991, abandoned, which is a division of Ser. No. 13,477, Feb. 11, 1987, Pat. No. 5,079,342, which is a continuation-in-part of Ser. No. 3,764, Jan. 16, 1987, Pat. No. 5,051,496, which is a continuation-in-part of Ser. No. 933,184, Nov. 21, 1986, abandoned, which is a continuation-in-part of Ser. No. 916,080, Oct. 6, 1986, abandoned, which is a continuation-in-part of Ser. No. 835,228, Mar. 3, 1986, Pat. No. 4,839,288.

[30] Foreign Application Priority Data

| Jan. 22, 1986 | [FR] | France | 86 00911 |
| Feb. 6, 1986 | [FR] | France | 86 01635 |
| Feb. 13, 1986 | [FR] | France | 86 01985 |
| Mar. 18, 1986 | [FR] | France | 86 03881 |
| Mar. 24, 1986 | [FR] | France | 86 04215 |

[51] Int. Cl.$^6$ .......... G01N 33/53; G01N 33/564; A61K 35/21; G12P 21/06
[52] U.S. Cl. .......... 435/7.1; 424/188.1; 424/208.1; 435/69.1; 435/172.3; 435/974; 435/5; 536/23.72
[58] Field of Search .......... 435/5, 7.1, 69.1, 435/172.3, 974; 530/350; 424/188.1, 208.1; 536/23.72

[56] References Cited

U.S. PATENT DOCUMENTS

| 4,629,783 | 12/1986 | Cosand . |
| 4,839,288 | 6/1989 | Montagnier et al. . |
| 5,079,342 | 1/1992 | Alizon et al. . |

FOREIGN PATENT DOCUMENTS

| 0316695B1 | 3/1993 | European Pat. Off. . |
| WO85/04897 | 11/1985 | WIPO . |

OTHER PUBLICATIONS

Gallo et al., "HIV/HTLV gene nomenclature", Nature 333:564 (1988).
Laurence, J., "Summary of HIV–1 and HIV–2 nomenclature", AIDS Res. Hum. Retro. 4:vii–viii (1988).
(a) Clavel et al., "Molecular cloning and polymorphism of the human immunodeficiency virus type 2", Nature 324:691–695 (1986).
Clavel et al., "Isolation of a new Human Retrovirus from West African Patients with AIDS," Science, 233, pp. 343–346 (1986).
Allan et al., "Major Glycoprotein Antigens That Induce Antibodies in AIDS Patients Are Encoded by HTLV–III," Sceience, 228, pp. 1091–1094 (1985).
Chang et al., "Detection of Antibodies to Human T–Cell Lymphotropic Virus–III (HTLV–III) with an Immunoassay Employing a Recombinant Escherichia coli–Derived Viral Antigenic Peptide," Bio/Technology, 3, pp. 905–909 (1985).
Kanki et al., "Isolation of T–lymphotropic Retrovirus Related to HTLV–III/LAV from Wild–Caught African Green Monkeys," Science, 230, pp. 951–954 (1985).
Kanki et al., "Serologic Identification and Characterization of a Macaque T–lymphotropic Retrovirus Closely Related to HTLV–III," Science, 228, pp. 1199–1201 (1985).
Clavel et al., "LAV TypeII: A Second Retrovirus Associated With AIDS in West Africa," C. R. Acad. Sc. Paris, Serie III, 302, pp. 485–488 (1986).
Klatzmann et al., "T–lymphocyte T4 Molecule Behaves As The Receptor For Human Retrovirus LAV," Nature, 312, pp. 767–768 (1984).
Daniel et al., "Isolation of T–Cell Tropic HTLV–III–like Retrovirus from Macaques," Science, 228, pp. 1201–1204 (1985).
Barin et al., "Serological Evidence For Virus Related To Simian T–lymphotropic Retrovirus III in Residents of West Africa," The Lancet, pp. 1387–1389 (Dec. 21/28, 1985).
Sandstrom et al., "Antiviral Therapy in AIDS Clinical Pharmacological Properties and Therapeutic Experience to Date," Drugs, 34, pp. 372–390 (1987).
Mitsuya et al., "Protection of T Cells Against Infectivity and Cytopathic Effect of HTLV–III In Vitro," Retroviruses in Human Lymphoma/Leukemia, M. Miwa et al., eds., pp. 277–288 (Japan Science Press, Tokyo, 1985).

*Primary Examiner*—Christine M. Nucker
*Assistant Examiner*—Jeffrey S. Parkin
*Attorney, Agent, or Firm*—Finnegan, Henderson, Farabow, Garrett & Dunner

[57] ABSTRACT

A novel lentivirus, designated the human immunodeficiency virus type 2 (HIV-2$_{ROD}$), was isolated from West African patients with acquired immune deficiency syndrome (AIDS). A recombinant lambda phage library was constructed from HIV-2$_{ROD}$-infected CEM genomic DNA. Overlapping molecular clones were obtained and the nucleotide sequence of the complete 9.5-kilobase (kb) HIV-2$_{ROD}$ genome ascertained. The genetic organization of HIV-2 is analogous to that of other retroviruses and consists of the 5'LTR-gag-pol-central region-env-nef-3'LTR. The central region also encodes for the regulatory proteins Tat and Rev, as well as the ancillary proteins Vif, Vpr, and Vpx. The proteins encoded by this proviral clone will provide novel immunologic, biochemic, and diagnostic reagents useful for the detection of HIV-2.

14 Claims, 5 Drawing Sheets

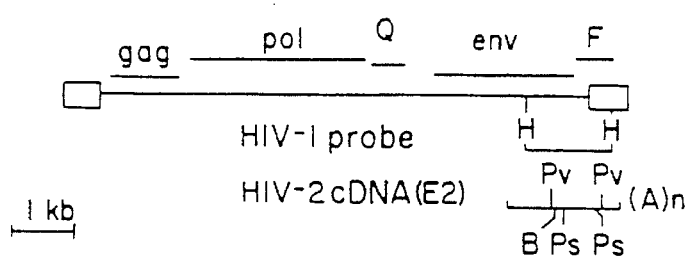

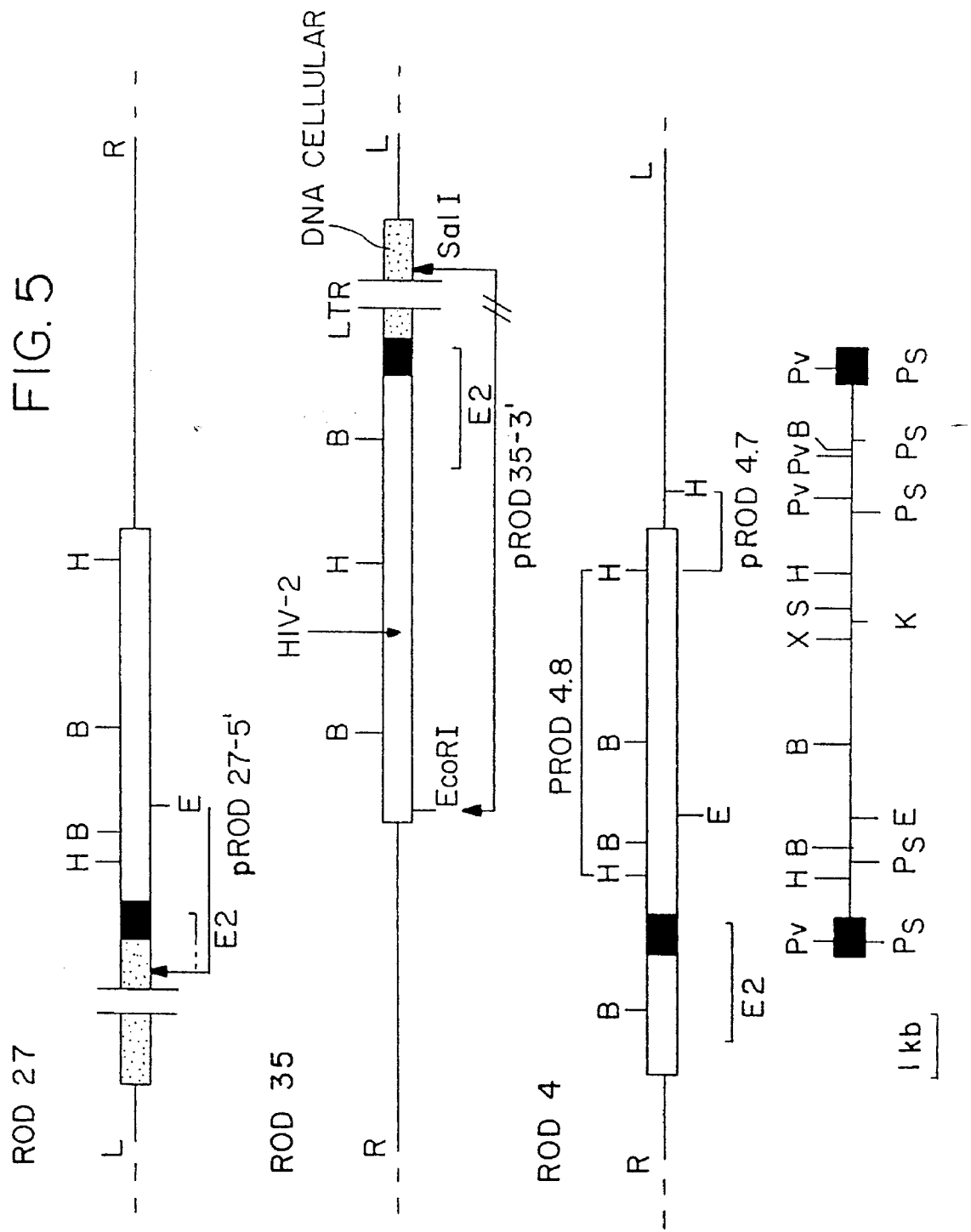

PEPTIDES OF HUMAN IMMUNODEFICIENCY VIRUS TYPE 2 (HIV-2) AND IN VITRO DIAGNOSTIC METHODS AND KITS EMPLOYING THE PEPTIDES FOR THE DETECTION OF HIV-2

This is a division of application Ser. No. 07/810,908 abandoned, filed Dec. 20, 1991, which is a divisional of application Ser. No. 07/752,368 abandoned, filed Sep. 3, 1991, which is a divisional of application Ser. No. 07/013,477, filed Feb. 11, 1987, (now U.S. Pat. No. 5,079,342), which is a CIP of application Ser. No. 07/003,764, filed Jan. 16, 1987, (now U.S. Pat. No. 5,051,496), which is a CIP of application Ser. No. 06/933,184 abandoned, filed Nov. 21, 1986, which is a CIP of application Ser. No. 06/916,080 abandoned, filed Oct. 6, 1986, which is a CIP of application Ser. No. 06/835,228, filed Mar. 3, 1986, (now U.S. Pat. No. 4,839,288).

BACKGROUND OF THE INVENTION

The disclosures of each of these predecessor applications are expressly incorporated herein by reference.

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECACC under No. 87.001.001 on Jan. 9, 1987. A second LAV-II isolate was deposited at CNCM on Feb. 21, 1986 under Accession No. I-532 and has also been deposited at the British ECACC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to:

(1) Southern blot procedures to identify viral DNA which may or may not be digested with restriction enzymes;
(2) Northern blot techniques to identify viral RNA extracted from cells; and
(3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by ultra-centrifugation as accomplished in the "CYTODOT" procedure as described in a booklet published by Schleicher and Schull.

In an alternate embodiment, the kit contains the polypeptides created using these cloned DNA sequences. The polypeptides are capable of reacting with antibodies to the HIV-2 virus present in sera of infected individuals, thus yielding an immunodiagnostic complex.

In accordance with a further object of the present invention, a peptide is provided as described above, either alone or conjugated to a carrier molecule, the peptide being capable of eliciting the production of an antibody to the peptide, and said antibody is capable of forming an effective immunocomplex with the entire HIV-2 retrovirus or with its corresponding proteins.

To further achieve the objects of the invention, a vaccinating agent is provided which comprises at least one peptide selected from the polypeptide expression products of the viral DNA in admixture with suitable carriers, adjuvents stabilizers.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 1 generally depicts the nucleotide sequence of a cloned complementary DNA (cDNA) to the genomic RNA of HIV-2. FIG. 1A depicts the genetic organization of HIV-1, position of the HIV-1 HindIII fragment used as a probe to screen the cDNA library, and restriction map of the HIV-2 cDNA clone, E2. FIG. 1B depicts the nucleotide sequence of the 3' end of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. U.S.A. 80: 726–730 (1983), specifically incorporated herein by reference. The U3-R junction in HIV-1 is indicated and the poly A addition signal and potential TATA promoter regions are boxed. In FIG. 1A, the symbols B, H, Ps and Pv refer to the restriction sites BamHI, HindIII, PstI and PvuII, respectively.

FIG. 2 generally depicts the HIV-2 specificity of the E2 clone.

FIG. 3 generally depicts a restriction map of the HIV-2 ROD genome and its homology to HIV-1. In FIG. 3A, the open boxes represent viral sequences, the LTR are filled, and the dotted boxes represent cellular flanking sequences (not mapped). Only some characteristic restriction enzyme sites are indicated. λROD 27 and λROD 35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 4 generally depicts the restriction map polymorphism in different HIV-2 isolates and shows comparison of HIV-2 to SIV.

FIG. 5 depicts the position of derived plasmids from λROD 27, λROD 35 and λROD 4.

DETAILED DESCRIPTION OF THE PREFERRED EMBODIMENTS

Figures 2A, 2B, 2C, 2D:
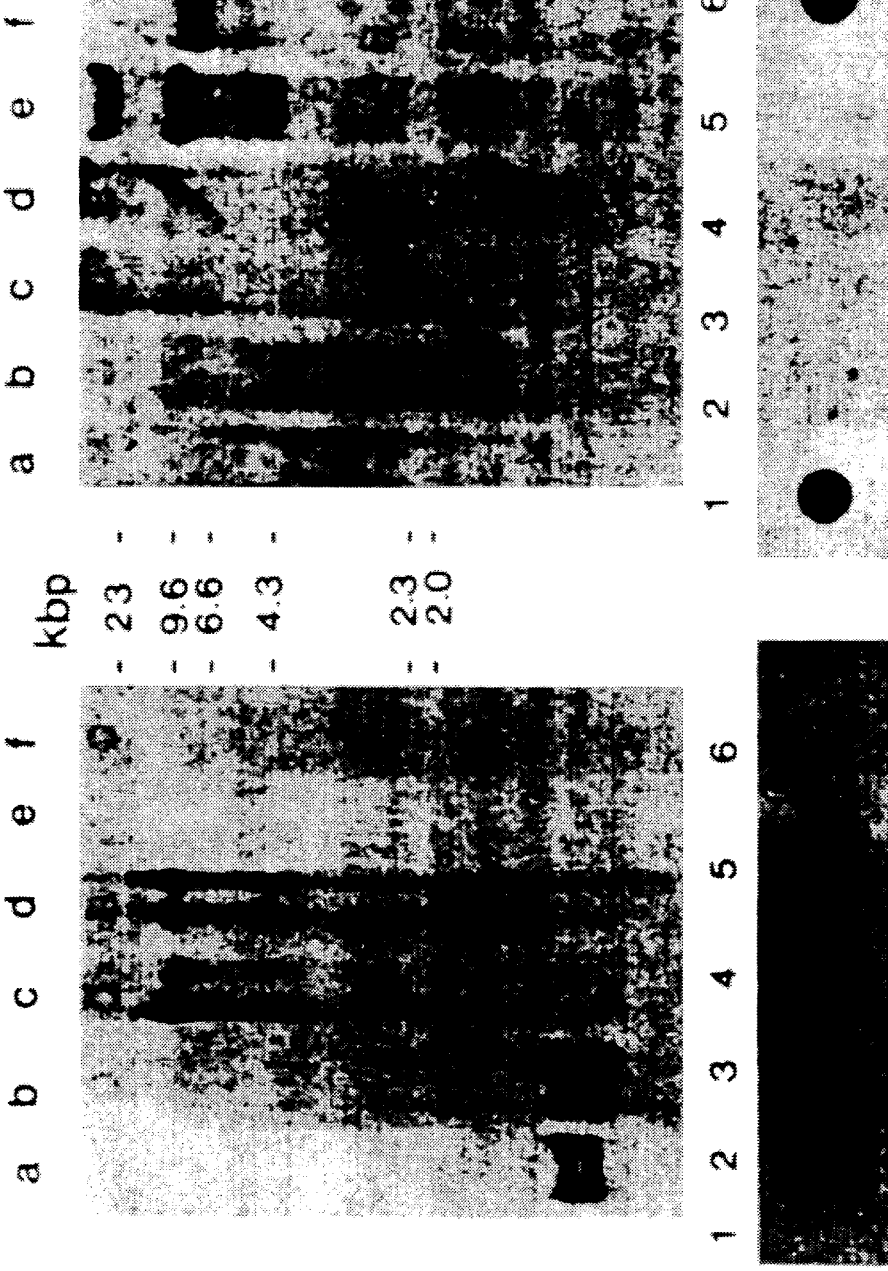
FIG. 2A and B are line drawings representing Southern Blots of DNA extracted from CEM cells infected with the following isolates: HIV-2$_{ROD}$ (a,c), HIV-2$_{DUL}$ (b,d), and HIV-1$_{BRU}$ (e,f). DNA in lanes a,b,f was Pst I digested; in c,d,e DNA was undigested.
FIG. 2C and D are line drawings representing dot blot hybridization of pelleted virions from CEM cells infected by the HIV-1$_{BRU}$(1), Simian Immunodeficiency Virus (SIV) isolate Mm 142–83 (3), HIV-2$_{DUL}$ (4), HIV-2$_{ROD}$ (5), and HIV-1$_{ELI}$ (6). Dot 2 is a pellet from an equivalent volume of supernatant from uninfected CEM. Thus, FIG. 2A and C depict hybridization with the HIV-2 cDNA (E2) and FIG. 2B and D depict hybridization to an HIV-1 probe consisting of a 9 Kb SacI insert from HIV-1 BRU(clone lambda J 19).

Reference will now be made in detail to the presently preferred embodiments of the invention, which together with the following examples, serve to explain the principles of the invention.

The genetic structure of the HIV-2 virus has been analyzed by molecular cloning according to the method set forth herein and in the Examples. A restriction map of the genome of this virus is included in FIG. 5. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and pol genes were conducted. These hybridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M 13 tg 130 bacteriophage vector. A collection of $10^4$ M13 recombinant phages was obtained and screened in situ with an HIV-1 probe spanning 1.5 kb. of the 3' end of the $LAV_{BRU}$ isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1 B. Indeed, only about 50% of the nucleotides could be aligned and about a hundred insertions/deletions need to be introduced. In comparison, the homology of the corresponding domains in HIV-1 isolates from U.S.A. and Africa is greater than 95% and no insertions or deletions are seen.

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with HIV-$2_{ROD}$.

About $2\times10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
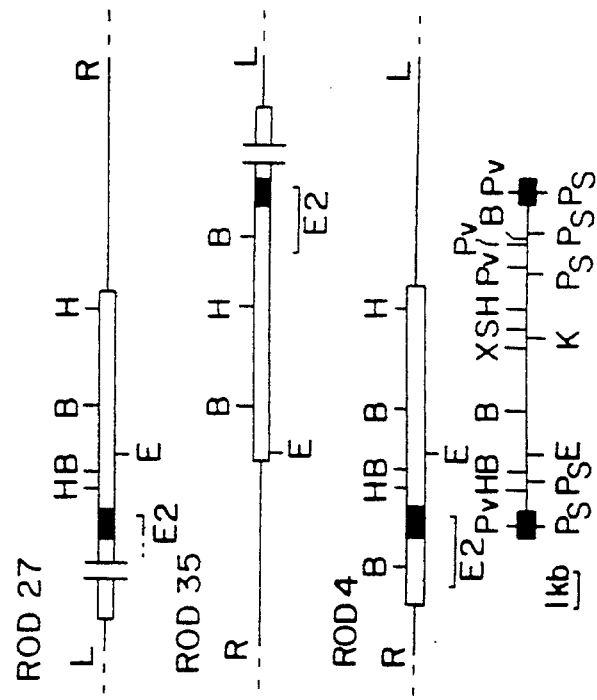
FIG. 3A specifically depicts the organization of three recombinant phage lambda clones, ROD 4, ROD 27, and ROD 35.
Figure 3B:
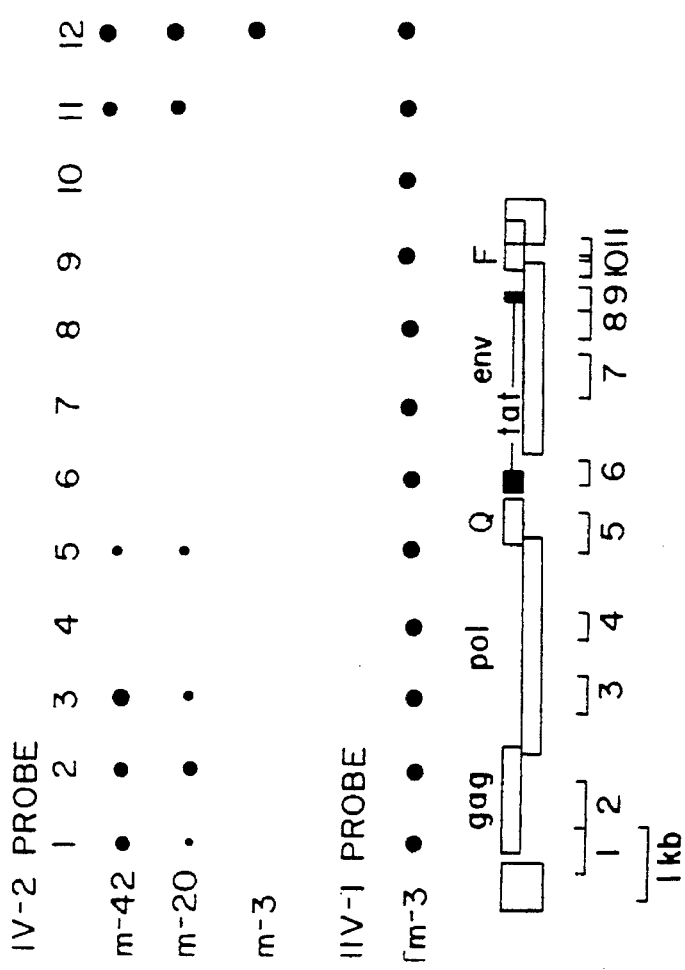
FIG. 3B specifically depicts dots 1-11 which correspond to the single-stranded DNA form of M13 subclones from the HIV-1$_{BRU}$ cloned genome (λJ19). Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2×SSC, 0.1% SDS at 25° C. (Tm −42° C.), 1×SSC, 0.1% SDS at 60° C. (Tm −20° C.), and 0.1×SSC, 0.1% SDS at 60° C. (Tm −3° C.) and exposed overnight. A duplicate dot was hybridized and washed in stringent conditions (as described in Example 2) with the labelled lambda J19 clone carrying the complete HIV-1$_{BRU}$ genome. HIV-1 and HIV-2 probes were labelled the same specific activity ($10^8$ cpm/ g.).

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A.

Fragments of the lambda clones were subcloned into a plasmid vector p UC 18.

Plasmid pROD 27-5' is derived from λROD 27 and contains the 5' 2 Kb of the HIV-2 genome and cellular flanking sequences (5' LTR and 5' viral coding sequences to the EcoRI site)

Plasmid p ROD 4-8 is derived from λROD 4 and contains the about 5 Kb HindIII fragment that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamHI and HindIII cloning sites.

Plasmid pROD 35 contains all the HIV-2 coding sequences 3' to the EcoRI site, the 3' LTR and about 4 Kb of cellular flanking sequences.

Plasmid pROD 27-5 and pROD 35 in E. coli strain HB 101 are deposited respectively under No. I-627 and I-628 at the CNCM, and have also been deposited at the NCIB (British Collection). These plasmids are depicted in FIG. 5. Plasmids pROD 4-7 and pROD 4-8 in E. coli strain TG1 are deposited respectively under No. 1-627 and 1-628 at the CNCM.

To reconstitute the complete HIV-2 ROD genome, pROD 35 is linearized with EcoRI and the EcoRI insert of pROD 27-5' is ligated in the correct orientation into this site.

The relationship of HIV-2 to other human and simian retroviruses was surmised from hybridization experiments.

The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm-42° C.), the hybridization of HIV-1 and 2 was restricted to a fraction of their genomes, principally the gag gene (dots 1 and 2), the reverse transcriptase domain in pol (dot 3), the end of pol and the Q (also called Vif) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1, as are African isolates from Zaire described by Alizon et al., Cell 40:63–74 (1986).

It was observed that HIV-2 is related more closely to the Simian Immunodeficiency Virus (SIV) than it is to HIV-1. This correlation has been described by F. Clavel et al. in C.R. Acad. Sci. (Paris) 302:485–488 (1986) and F. Clavel et al. in Science 233:343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described by M.D. Daniel et al. in Science 288:1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the gag or pol genes. Under the same conditions, HIV-1 derived probes do not detect the SIV genome as shown in FIG. 2, D.

In Southern blots of DNA from SIV-infected cells, a restriction pattern clearly different from HIV-2$_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

Figure 4B:
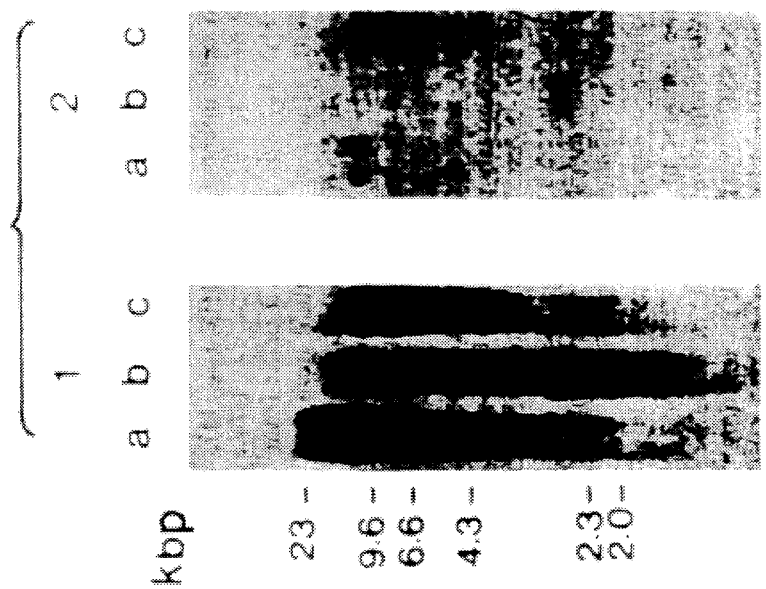
FIG. 4B is a line drawing depicting DNA from HUT 78 (a human T lymphoid cell line) cells infected with STLV3 MAC isolate Mm 142–83. The same amounts of DNA and enzymes were used as indicated in panel A. Hybridization was performed with the same probe as in A, but in non-stringent conditions. As described in Example 1 washing was for one hour in 2×SSC, 0.1% SDS at 40° C. (panel 1) and after exposure, the same filter was re-washed in 0.1× SSC, 0.1% SDS at 60° C. (panel 2). The autoradiographs were obtained after overnight exposition with intensifying screens.
Figure 4A:
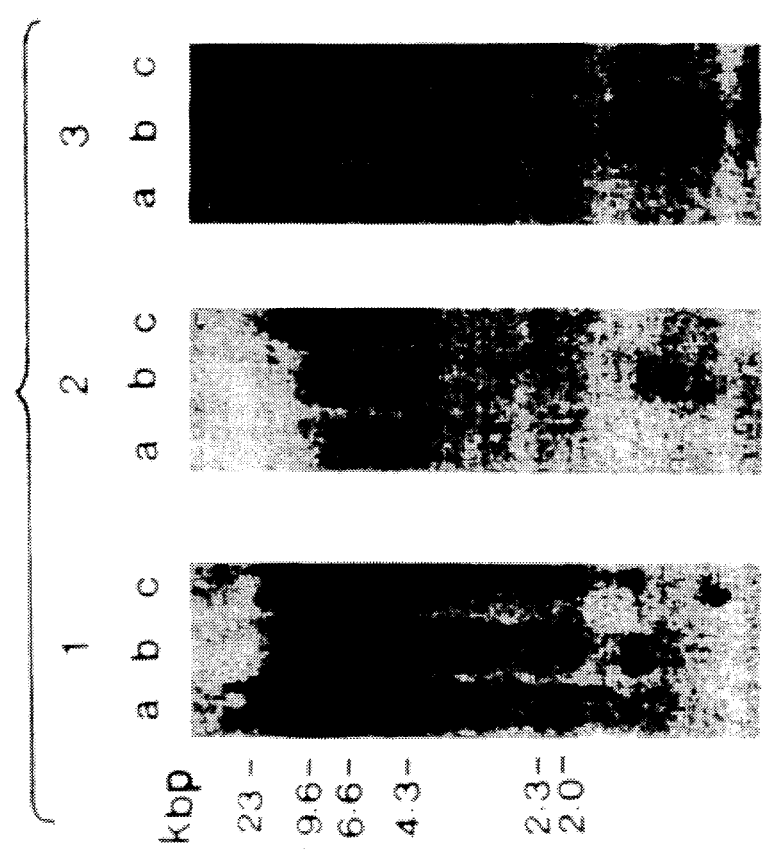
FIG. 4A is a line drawing depicting DNA (20 μg per lane) from CEM cells infected by the isolate HIV-2$_{DUL}$ (panel 1) or peripheral blood lymphocytes (PBL) infected by the isolates HIV-2$_{GOM}$ (panel 2) and HIV-2$_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb HindIII fragment of λROD 4, labelled to $10^9$ cpm/μg.

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-2$_{ROD}$. It is very likely that these differences at the nucleotide level are accompanied by variations in the amino-acid sequence of the viral proteins, as evidenced in the case of HIV-1 and described by M. Alizon et al. in Cell 46:63–74 (1986), specifically incorporated herein by reference. It is also to be expected that the various isolates of HIV-2 will exhibit amino acid heterogeneities. See, for example, Clavel et al., Nature 324 (18):691–695 (1986), specifically incorporated herein by reference.

Further, the characterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1

Cloning of a cDNA Complementary to Genomic RNA From HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Gubler and Hoffman in Gene, 25: 263–269 (1983), specifically incorporated herein by reference, using a commercial cDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the E. coli TG1 strain. Recombinant plaques ($10^4$) were screened in situ on replica filters with the 1.5 kb. HindIII fragment from clone J19, corresponding to the 3' part of the genome of the $LAV_{BRU}$ isolate of HIV-1, $^{32}P$ labelled to a specific activity of $10^9$ cpm μg. The filters were prehybridized in 5×SSC, 5×Denhardt solution, 25% formamide, and denatured salmon sperm DNA (100 μg/ml) at 37° C. for 4 hours and hybridized for 16 hours in the same buffer (Tm −42° C.) plus $4×10^7$ cpm of the labelled probe ($10^6$ cpm/ml. of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method described in Proc. Nat'l. Acad. Sci. USA, 74: 5463–5467 (1977) of Sanger et al.

Example 2

Hybridization of DNA from HIV-1 and HIV-2 Infected Cells and RNA from HIV-1 and 2 and SIV Virons With a Probe Derived From an HIV-2 Cloned cDNA

DNA was extracted from infected CEM cells continuously producing HIV-1 or 2. The DNA digested with 20 μg of PstI or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity. Prehybridization was done in 50% formamide, 5×SSC, 5×Denhardt solution, and 100 mg./ml. denatured salmon sperm DNA for 4 hours at 42° C. Hybridization was performed in the same buffer plus 10% Dextran sulphate, and $10^6$ cpm/ml. of the labelled E2 insert (specific activity $10^9$ cpm/μg) for 16 hours at 42° C. Washing was in 0.1×SSC, 0.1% SDS for 2×30 mn. After exposition for 16 hours with intensifying screens, the Southern blot was dehybridized in 0.4N NaOH, neutralized, and rehybridized in the same conditions to the HIV-1 probe labelled to $10^9$ cpm/μg.

Example 3

Cloning in Lambda Phage of the Complete Provirus DNA of HIV-2

DNA from the HIV-$2_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques ($2×10^6$) obtained after in vitro packaging and plating on E. coli LA 101 strain were screened in situ with the insert from the E2 cDNA clone. Approximately 10 positive clones were plaque purified and propagated on E. coli C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4

Complete Genomic Sequence of the ROD HIV-2 Isolate

Experimental analysis of the HIV-2 ROD isolate yielded the following sequence which represents the complete genome of this HIV-2 isolate. Genes and major expression products identified within the following sequence are indicated by nucleotides numbered below:

1) GAG gene (546-2111) expresses a protein product (also called gag precursor protein) having a molecular weight of around 55 KD and is cleaved into the following proteins:
   a) p 16 (also called p 16/matrix protein) (546-950)
   b) p 26 (also called p 26/capsid protein) (951-1640)
   c) p 12 (also called p 12/nucleocapsid protein) (1701-2111)
2) polymerase (also called polymerase precursor protein) (1829-4936)
3) Q protein (4869-5513) (also called Vif)
4) R protein (5682-5996) (also called Vpr)
5) X protein (5344-5679) (also called Vpx)
6) Y protein (5682-5996)
7) Env protein (also called env precursor protein) (6147-8720)
8) F protein (8557-9324) (also called Nef)
9) TAT gene (5845-6140 and 8307-8400) is expressed by two exons separated by introns.
10) ART protein (also called Rev) (6071-6140 and 8307-8536) is similarly the expression product of two exons.
11) LTR:R (1-173 and 9498-9671)
12) U5 (174-299)
13) U3 (8942-9497)

It will be known to one of skill in the art that the absolute numbering which has been adopted is not essential. For example, the nucleotide within the LTR which is designated as "1" is a somewhat arbitrary choice. What is important is the sequence information provided.

GGTCGCTCTGCGGAGAGGCTGGCAGATTGAGCCCTGGGAGGTTCTCTCCAGCACTAGCAG

GTAGAGCCTGGGTGTTCCCTGCTAGACTCTCACCAGCACTTGGCCGGTCCTGGGCAGACG
                                            100

GCCCCACGCTTGCTTGCTTAAAAACCTCTTAATAAAGCTGCCAGTTAGAAGCAAGTTAAG

TGTGTGCTCCCATCTCTCCTAGTCGCCGCCTGGTCATTCGGTGTTCACCTGAGTAACAAG
                      200

ACCCTGGTCTGTTAGGACCCTTCTTGCTTTGGGAAACCGAGGCAGGAAAATCCCTAGCAG
                                                            300

GTTGGCGCCTGAACAGGGACTTGAAGAAGACTGAGAAGTCTTGGAACACGGCTGAGTGAA

GGCAGTAAGGGCGGCAGGAACAAACCACGACGGAGTGCTCCTAGAAAGGCGCGGGCCGAG
                            400

GTACCAAAGGCAGCGTGTGGAGCGGGAGGAGAAGAGGCCTCCGGGTGAAGGTAAGTACCT

ACACCAAAAACTGTAGCCGAAAGGGCTTGCTATCCTACCTTTAGACAGGTAGAAGATTGT
                500

Met Gly Ala Arg Asn Ser Val Leu Arg Gly Lys Lys Ala Asp Glu Leu Glu Arg Ile
GGGAGATGGGCGCGAGAAACTCCGTCTTGAGAGGGAAAAAAGCAGATGAATTAGAAAGAA
                                                            600

Arg Leu Arg Pro Gly Gly Lys Lys Lys Tyr Arg Leu Lys His Ile Val Trp Ala Ala Asn
TCAGGTTACGGCGCGGCCGAAAGAAAAAGTACAGGCTAAAACATATTGTGTGGGCAGCGA

Lys Leu Asp Arg Phe Gly Leu Ala Glu Ser Leu Leu Glu Ser Lys Glu Gly Cys Gln Lys
ATAAATTGGACAGATTCGGATTAGCAGAGAGCCTGTTGGAGTCAAAAGAGGGTTGTCAAA
                                    700

Ile Leu Thr Val Leu Asp Pro Met Val Pro Thr Gly Ser Glu Asn Leu Lys Ser Leu Phe
AAATTCTTACAGTTTTAGATCCAATGGTACCGACAGGTTCAGAAAATTTAAAAAGTCTTT

Asn Thr Val Cys Val Ile Trp Cys Ile His Ala Glu Glu Lys Val Lys Asp Thr Glu Gly
TTAATACTGTCTGCGTCATTTGGTGCATACACGCAGAAGAGAAAGTGAAAGATACTGAAG
                        800

Ala Lys Gln Ile Val Arg Arg His Leu Val Ala Glu Thr Gly Thr Ala Glu Lys Met Pro
GAGCAAAACAAATAGTGCGGAGACATCTAGTGGCAGAAACAGGAACTGCAGAGAAAATGC
                                                            900

Ser Thr Ser Arg Pro Thr Ala Pro Ser Ser Glu Lys Gly Gly Asn Tyr Pro Val Gln His
CAAGCACAAGTAGACCAACAGCACCATCTAGCGAGAAGGGAGGAAATTACCCAGTGCAAC

Val Gly Gly Asn Tyr Thr His Ile Pro Leu Ser Pro Arg Thr Leu Asn Ala Trp Val Lys
ATGTAGGCGGCAACTACACCCATATACCGCTGAGTCCCCGAACCCTAAATGCCTGGGTAA
                                        1000

Leu Val Glu Glu Lys Lys Phe Gly Ala Glu Val VaL Pro Gly Phe Gln Ala Leu Ser Glu
AATTAGTAGAGGAAAAAAAGTTCGGGGCAGAAGTAGTGCCAGGATTTCAGGCACTCTCAG

Gly Cys Thr Pro Tyr Asp Ile Asn Gln Met Leu Asn Cys Val Gly Asp His Gln Ala Ala
AAGGCTGCACGCCCTATGATATCAACCAAATGCTTAATTGTGTGGGCGACCATCAAGCAG
                            1100

Met Gln Ile Ile Arg Glu Ile Ile Asn Glu Glu Ala Ala Glu Trp Asp Val Gln His Pro
CCATGCAGATAATCAGGGAGATTATCAATGAGGAAGCAGCAGAATGGGATGTGCAACATC
                                                            1200

Ile Pro Gly Pro Leu Pro Ala Gly Gln Leu Arg Glu Pro Arg Gly Ser Asp Ile Ala Gly
CAATACCAGGCCCCTTACCAGCGGGGCAGCTTAGAGAGCCAAGGGGATCTGACATAGCAG

Thr Thr Ser Thr Val Glu Glu Gln Ile Gln Trp Met Phe Arg Pro Gln Asn Pro Val Pro
GGACAACAAGCACAGTAGAAGAACAGATCCAGTGGATGTTTAGGCCACAAAATCCTGTAC
                                    1300

Val Gly Asn Ile Tyr Arg Arg Trp Ile Gln Ile Gly Leu Gln Lys Cys Val Arg Met Tyr
CAGTAGGAAACATCTATAGAAGATGGATCCAGATAGGATTGCAGAAGTGTGTCAGGATGT

-continued

Asn Pro Thr Asn Ile  Leu Asp Ile  Lys Gln Gly Pro Lys Glu Pro Phe Gln Ser  Tyr  Val
ACAACCCGACCAACATCCTAGACATAAAACAGGGACCAAAGGAGCCGTTCCAAAGCTATG
                    1400

Asp Arg Phe Tyr Lys Ser  Leu Arg Ala Glu Gln Thr Asp Pro Ala  Val Lys Asn Trp Met
TAGATAGATTCTACAAAAGCTTGAGGGCAGAACAAACAGATCCAGCAGTGAAGAATTGGA
                                                                1500

Thr Gln Thr Leu Leu Val Gln Asn Ala Asn Pro Asp Cys Lys Leu Val Leu Lys Gly Leu
TGACCCAAACACTGCTAGTACAAAATGCCAACCCAGACTGTAAATTAGTGCTAAAAGGAC

Gly Met Asn Pro Thr Leu Glu Glu Met Leu Thr Ala Cys Gln Gly Val Gly Gly Pro Gly
TAGGGATGAACCCTACCTTAGAAGAGATGCTGACCGCCTGTCAGGGGGTAGGTGGGCCAG
                            1600

Gln Lys Ala Arg Leu Met Ala Glu Ala Leu Lys Glu Val Ile  Gly Pro Ala Pro Ile  Pro
GCCAGAAAGCTAGATTAATGGCAGAGGCCGTGAAAGAGGTCATAGGACCTGCCCCTATCC

Phe Ala Ala Ala Gln Gln Arg Lys Ala Phe Lys Cys Trp Asn Cys Gly Lys Glu Gly His
CATTCGCAGCAGCCCAGCAGAGAAAGGCATTTAAATGCTGGAACTGTGGAAAGGAAGGGC
                        1700

Ser Ala Arg Gln Cys Arg Ala Pro Arg Arg Gln Gly Cys Trp Lys Cys Gly Lys Pro Gly
ACTCGGCAAGACAATGCCGAGCACCTAGAAGGCAGGGCTGCTGGAAGTGTGGTAAGCCAG
                                                        1800

Thr Gly Arg Phe Phe Arg Thr Gly Pro Leu Gly
His Ile  Met Thr Asn Cys Pro Asp Arg Gln Ala Gly Phe Leu Gly Leu Gly Pro Trp Gly
GACACATCATGACAAACTGCCCAGATAGACAGGCAGGTTTTTTAGGACTGGGCCCTTGCG

Lys Glu Ala Pro Gln Leu Pro Arg Gly Pro Ser  Ser  Ala Gly Ala Asp Thr Asn Ser  Thr
  Lys Lys Pro Arg Asn Phe Pro  Val Ala Gln Val Pro Gln Gly Leu Thr Pro Thr Ala Pro
GAAAGAAGCCCCGCAACTTCCCCGTGGCCCAAGTTCCGCAGGGGCTGACACCAACAGCAC
                                    1900

Pro Ser Gly Ser Ser Ser Gly Ser Thr Gly Glu Ile  Tyr Ala Ala Arg Glu Lys Thr Glu
  Pro Val Asp Pro Ala Val Asp Leu Leu Glu Lys Tyr Met Gln Gln Gly Lys Arg Gln Arg
CCCCAGTGGATCCAGCAGTGGATCTACTGGAGAAATATATGCAGCAAGGGAAAAGACAGG

Arg Ala Glu Arg Glu Thr Ile  Gln Gly Ser Asp Arg Gly Leu Thr Ala Pro Arg Ala Gly
  Glu Gln Arg Glu Arg Pro Tyr Lys Glu Val Thr Glu Asp Leu Leu His Leu Glu Gln Gly
GAGAGCAGAGAGAGAGACCATACAAGGAAGTGACAGAGGACTTACTGCACCTCGAGCAGG
                    2000

Gly Asp Thr Ile  Gln Gly Ala Thr Asn Arg Gly Leu Ala Ala Pro Gln Phe Ser  Leu Trp
  Glu Thr Pro Tyr Arg Glu Pro Pro Thr Glu Asp Leu Leu His Leu Asn Ser  Leu Phe Gly
GGGAGACACCATACAGGGAGCCACCAACAGAGGACTTGCTGCACCTCAATTCTCTCTTTG
                                                        2100

Lys Arg Pro Val Val Thr Ala Tyr Ile  Glu Gly Gln Pro Val Glu Val Leu Leu Asp Thr
  Lys Asp Gln
GAAAAGACCAGTAGTCACAGCATACATTGAGGGTCAGCCAGTAGAAGTCTTGTTAGACAC

Gly Ala Asp Asp Ser  Ile  Val Ala Gly Ile  Glu Leu Gly Asn Asn Tyr Ser Pro Lys Ile
AGGGGCTGACGACTCAATAGTAGCAGGAATAGAGTTAGGGAACAATTATAGCCCAAAAAT
                                        2200

Val Gly Gly Ile  Gly Gly Phe Ile  Asn Thr Lys Glu Tyr Lys Asn Val Glu Ile  Glu Val
AGTAGGGGGAATAGGGGGATTCATAAATACCAAGGAATATAAAAATCTAGAAATAGAAGT

Leu Asn Lys Lys Val Arg Ala Thr Ile  Met Thr Gly Asp Thr Pro Ile  Asn Ile  Phe Gly
TCTAAATAAAAAGGTACGGGCCACCATAATGACAGGCGACACCCCAATCAACATTTTTGG
                    2300

Arg Asn Ile  Leu Thr Ala Leu Gly Met Ser Leu Asn Leu Pro Val Ala Lys Val Glu Pro
CAGAAATATTCTGACAGCCTTAGGCATGTCATTAAATCTACCAGTCGCCAAAGTAGAGCC
                                                            2400

Ile  Lys Ile  Met Leu Lys Pro Gly Lys Asp Gly Pro Lys Leu Arg Gln Trp Pro Leu Thr
AATAAAAATAATGCTAAAGCCAGGGAAAGATGGACCAAAACTGAGACAATGGCCCTTAAC

Lys Glu Lys Ile  Glu Ala Leu Lys Glu Ile  Cys Glu Lys Met Glu Lys Glu Gly Gln Leu
AAAAGAAAAAATAGAAGCACTAAAAGAAATCTGTGAAAAAATGGAAAAAGAAGGCCAGCT
                            2500

```
Glu Glu Ala Pro Pro Thr Asn Pro Tyr Asn Thr Pro Thr Phe Ala Ile  Lys Lys Lys Asp
AGAGGAAGCACCTCCAACTAATCCTTATAATACCCCCACATTTGCAATCAAGAAAAAGGA

Lys Asn Lys Trp Arg Met Leu Ile  Asp Phe Arg Glu Leu Asn Lys Val Thr Gln Asp Phe
CAAAAACAAATGGAGGATGCTAATAGATTTCAGAGAACTAAACAAGGTAACTCAAGATTT
                                      2600

Thr Glu Ile  Gln Leu Gly Ile  Pro His Pro Ala Gly Leu Ala Lys Lys Arg Arg Ile  Thr
CACAGAAATTCAGTTAGGAATTCCACACCCAGCAGGGTTGGCCAAGAAGAGAAGAATTAC
                                                                        2700

Val Leu Asp Val Gly Asp Ala Tyr Phe Ser Ile  Pro Leu His Glu Asp Phe Arg Pro Tyr
TGTACTAGATGTAGGGGATGCTTACTTTTCCATACCACTACATGAGGACTTTAGACCATA

Thr Ala Phe Thr Leu Pro Ser Val Asn Asn Ala Glu Pro Gly Lys Arg Tyr Ile  Tyr Lys
TACTGCATTTACTCTACCATCAGTGAACAATGCAGAACCAGGAAAAAGATACATATATAA
                                          2800

Val Leu Pro Gln Gly Trp Lys Gly Ser Pro Ala Ile  Phe Gln His Thr Met Arg Gln Val
AGTCTTGCCACAGGGATGGAAGGGATCACCAGCAATTTTTCAACACACAATGAGACAGGT

Leu Glu Pro Phe Arg Lys Ala Asn Lys Asp Val Ile  Ile  Ile  Gln Tyr Met Asp Asp Ile
ATTAGAACCATTCAGAAAAGCAAACAAGGATGTCATTATCATTCAGTACATGGATGATAT
                            2900

Leu Ile  Ala Ser Asp Arg Thr Asp Leu Glu His Asp Arg Val Val Leu Gln Leu Lys Glu
CTTAATAGCTAGTGACAGGACAGATTTAGAACATGATAGGGTAGTCCTGCAGCTCAAGGA
                                                                3000

Leu Leu Asn Gly Leu Gly Phe Ser Thr Pro Asp Glu Lys Phe Gln Lys Asp Pro Pro Tyr
ACTTCTAAATGGCCTAGGATTTTCTACCCCAGATGAGAAGTTCCAAAAAGACCCTCCATA

His Trp Met Gly Tyr Glu Leu Trp Pro Thr Lys Trp Lys Leu Gln Lys Ile  Gln Leu Pro
CCACTGGATGGGCTATGAACTATGGCCAACTAAATGGAAGTTGCAGAAAATACAGTTGCC
                                        3100

Gln Lys Glu Ile  Trp Thr Val Asn Asp Ile  Gln Lys Leu Val Gly Val Leu Asn Trp Ala
CCAAAAAGAAATATGGACAGTCAATGACATCCAGAAGCTAGTGGGTGTCCTAAATTGGGC

Ala Gln Leu Tyr Pro Gly Ile  Lys Thr Lys His Leu Cys Arg Leu Ile  Arg Gly Lys Met
AGCACAACTCTACCCAGGGATAAAGACCAAACACTTATGTAGGTTAATCAGAGGAAAAAT
                    3200

Thr Leu Thr Glu Glu Val Gln Trp Thr Glu Leu Ala Glu Ala Glu Leu Glu Glu Asn Arg
GACACTCACAGAAGAAGTACAGTGGACAGAATTACCAGAAGCAGAGCTAGAAGAAAACAG
                                                          3300

Ile  Ile  Leu Ser Gln Glu Gln Glu Gly His Tyr Tyr Gln Glu Glu Lys Glu Leu Glu Ala
AATTATCCTAAGCCAGGAACAAGAGGGACACTATTACCAAGAAGAAAAAGAGCTAGAAGC

Thr Val Gln Lys Asp Gln Glu Asn Gln Trp Thr Tyr Lys Ile  His Gln Glu Glu Lys Ile
AACAGTCCAAAAGGATCAAGAGAATCAGTGGACATATAAAATACACCAGGAAGAAAAAAT
                                              3400

Leu Lys Val Gly Lys Tyr Ala Lys Val Lys Asn Thr His Thr Asn Gly Ile  Arg Leu Leu
TCTAAAAGTAGGAAAATATGCAAAGGTGAAAAACACCCATACCAATGGAATCAGATTGTT

Ala Gln Val Val Gln Lys Ile  Gly Lys Glu Ala Leu Val Ile  Trp Gly Arg Ile  Pro Lys
AGCACAGGTAGTTCAGAAAATAGGAAAAGAAGCACTAGTCATTTGGGGACGAATACCAAA
                    3500

Phe His Leu Pro Val Glu Arg Glu Ile  Trp Glu Gln Trp Trp Asp Asn Tyr Trp Gln Val
ATTTCACCTACCAGTAGAGAGAGAAATCTGGGAGCAGTGGTGGGATAACTACTGGCAAGT
                                                      3600

Thr Trp Ile  Pro Asp Trp Asp Phe Val Ser Thr Pro Pro Leu Val Arg Leu Ala Phe Asn
GACATGGATCCCAGACTGGGACTTCGTGTCTACCCCACCACTGGTCAGGTTAGCGTTTAA

Leu Val Gly Asp Pro Ile  Pro Gly Ala Glu Thr Phe Tyr Thr Asp Gly Ser Cys Asn Arg
CCTGGTAGGGGATCCTATACCAGGTGCAGAGACCTTCTACACAGATGGATCCTGCAATAG
                                            3700

Gln Ser Lys Glu Gly Lys Ala Gly Tyr Val Thr Asp Arg Gly Lys Asp Lys Val Lys Lys
GCAATCAAAAGAAGGAAAAGCAGGATATGTAACAGATAGAGGGAAAGACAAGGTAAAGAA
```

-continued

```
Leu Glu Gln Thr Thr Asn Gln Gln Ala Glu Leu Glu Ala Phe Ala Met Ala Leu Thr Asp
ACTAGAGCAAACTACCAATCAGCAAGCAGAACTAGAAGCCTTTGCGATGGCACTAACAGA
                        3800

Ser Gly Pro Lys Val Asn Ile  Ile  Val Asp Ser Gln Tyr Val Met Gly Ile  Ser Ala Ser
CTCGGGTCCAAAAGTTAATATTATAGTAGACTCACAGTATGTAATGGGGATCAGTGCAAG
                                                                       3900

Gln Pro Thr Glu Ser Glu Ser Lys Ile  Val Asn Gln Ile  Ile  Glu Glu Met Ile  Lys Lys
CCAACCAACAGAGTCAGAAAGTAAAATAGTGAACCAGATCATAGAAGAAATGATAAAAAA

Glu Ala Ile  Tyr Val Ala Trp Val Pro Ala His Lys Gly Ile  Gly Gly Asn Gln Glu Val
GGAAGCAATCTATGTTGCATGGGTCCCAGCCCACAAAGGCATAGGGGGAAACCAGGAAGT
                                                4000

Asp His Leu Val Ser Gln Gly Ile  Arg Gln Val Leu Phe Leu Glu Lys Ile  Glu Pro Ala
AGATCATTTAGTGAGTCAGGGTATCAGACAAGTGTTGTTCCTGGAAAAAATAGAGCCCGC

Gln Glu Glu His Glu Lys Tyr His Ser Asn Val Lys Glu Leu Ser His Lys Phe Gly Ile
TCAGGAAGAACATGAAAAATATCATAGCAATGTAAAAGAACTGTCTCATAAATTTGGAAT
                                4100

Pro Asn Leu Val Ala Arg Gln Ile  Val Asn Ser Cys Ala Gln Cys Gln Gln Lys Gly Glu
ACCCAATTTAGTGGCAAGGCAAATAGTAAACTCATGTGCCCAATGTCAACAGAAAGGGGA
                                                                4200

Ala Ile  His Gly Gln Val Asn Ala Glu Leu Gly Thr Trp Gln Met Asp Cys Thr His Leu
AGCTATACATGGGCAAGTAAATGCAGAACTAGGCACTTGGCAAATGGACTGCACACATTT

Glu Gly Lys Ile  Ile  Ile  Val Ala Val His Val Ala Ser Gly Phe Ile  Glu Ala Glu Val
AGAAGGAAAGATCATTATAGTAGCAGTACATGTTGCAAGTGGATTTATAGAAGCAGAAGT
                                                4300

Ile  Pro Gln Glu Ser Gly Arg Gln Thr Ala Leu Phe Leu Leu Lys Leu Ala Ser Arg Trp
CATCCCACAGGAATCAGGAAGACAAACAGCACTCTTCCTATTGAAACTGGCAAGTAGGTG

Pro Ile  Thr His Leu His Thr Asp Asn Gly Ala Asn Phe Thr Ser Gln Glu Val Lys Met
GCCAATAACACACTTGCATACAGATAATGGTGCCAACTTCACTTCACAGGAGGTGAAGAT
                        4400

Val Ala Trp Trp Ile  Gly Ile  Glu Gln Ser Phe Gly Val Pro Tyr Asn Pro Gln Ser Gln
GGTAGCATGGTGGATAGGTATAGAACAATCCTTTGGAGTACCTTACAATCCACAGAGCCA
                                                                4500

Gly Val Val Glu Ala Met Asn His His Leu Lys Asn Glu Ile  Ser Arg Ile  Arg Glu Gln
AGGAGTAGTAGAAGCAATGAATCACCATCTAAAAAACCAAATAAGTAGAATCAGAGAACA

Ala Asn Thr Ile  Glu Thr Ile  Val Leu Met Ala Ile  His Cys Met Asn Phe Lys Arg Arg
GGCAAATACAATAGAAACAATAGTACTAATGGCAATTCATTGCATGAATTTTAAAAGAAG
                        .                       4600

Gly Gly Ile  Gly Asp Met Thr Pro Ser Glu Arg Leu Ile  Asn Met Ile  Thr Thr Glu Gln
GGGGGGAATAGGGGATATGACTCCATCAGAAAGATTAATCAATATGATCACCACAGAACA

Glu Ile  Gln Phe Leu Gln Ala Lys Asn Ser Lys Leu Lys Asp Phe Arg Val Tyr Phe Arg
AGAGATACAATTCCTCCAAGCCAAAAATTCAAAATTAAAAGATTTTCGGGTCTATTTCAG
                        4700

Glu Gly Arg Asp Gln Leu Trp Lys Gly Pro Gly Glu Leu Leu Trp Lys Gly Glu Gly Ala
AGAAGGCAGAGATCAGTTGTGGAAAGGACCTGGGGAACTACTGTGGAAAGGAGAAGGAGC
                                                                4800

Val Leu Val Lys Val Gly Thr Asp Ile  Lys Ile  Ile  Pro Arg Arg Lys Ala Lys Ile  Ile
AGTCCTAGTCAAGGTAGGAACAGACATAAAAATAATACCAAGAAGGAAAGCCAAGATCAT

Arg Asp Tyr Gly Gly Arg Gln Glu Met Asp Ser Gly Ser His Leu Glu Gly Ala Arg Glu
                 Met Glu Glu Asp Lys Arg Trp Ile  Val Val Pro Thr Trp Arg Val Pro Gly Arg
CAGAGACTATGGAGGAAGACAAGAGATGGATAGTGGTTCCCACCTGGAGGGTGCCAGGGA
                                                4900

Asp Gly Glu Met Ala
 Met Glu Lys Trp His Ser Leu Val Lys Tyr Leu Lys Tyr Lys Thr Lys Asp Leu Glu Lys
GGATGGAGAAATGGCATAGCCTTGTCAAGTATCTAAAATACAAAACAAAGGATCTAGAAA
```

-continued

```
  Val Cys Tyr Val Pro His His Lys Val Gly Trp Ala Trp Trp Thr Cys Ser Arg Val Ile
AGGTGTGCTATGTTCCCCACCATAAGGTGGGATGGGCATGGTGGACTTGCAGCAGGGTAA
                        5000

Phe Pro Leu Lys Gly Asn Ser His Leu Glu Ile  Gln Ala Tyr Trp Asn Leu Thr Pro Glu
TATTCCCATTAAAAGGAAACAGTCATCTAGAGATACAGGCATATTGGAACTTAACACCAG
                                                            5100

Lys Gly Trp Leu Ser Ser Tyr Ser Val Arg Ile  Thr Trp Tyr Thr Glu Lys Phe Trp Thr
AAAAAGGATGGCTCTCCTCTTATTCAGTAAGAATAACTTGGTACACAGAAAAGTTCTGGA

Asp Val Thr Pro Asp Cys Ala Asp Val Leu Ile  His Ser Thr Tyr Phe Pro Cys Phe Thr
CAGATGTTACCCCAGACTGTGCAGATGTCCTAATACATAGCACTTATTTCCCTTGCTTTA
                                         5200

Ala Gly Glu Val Arg Arg Ala Ile  Arg Gly Glu Lys Leu Leu Ser Cys Cys Asn Tyr Pro
CAGCAGGTGAAGTAAGAAGAGCCATCAGAGGGGAAAAGTTATTGTCCTGCTGCAATTATC

Arg Ala His Arg Ala Gln Val Pro Ser Leu Gln Phe Leu Ala Leu Val Val Val Gln Gln
CCCGAGCTCATAGAGCCCAGGTACCGTCACTTCAATTTCTGGCCTTAGTGGTAGTGCAAC
                       5300

Met Thr Asp Pro Arg Glu Thr Val Pro Pro Gly Asn Ser Gly Glu Glu Thr Ile  Gly
  Asn Asp Arg Pro Gln Arg Asp Ser Thr Thr Arg Lys Gln Arg Arg Arg Asp Tyr Arg Arg
AAAATGACAGACCCCAGAGAGACAGTACCACCAGGAAACAGCGGCGAAGAGACTATCGGA
                                                            5400

Glu Ala Phe Ala Trp Leu Asn Arg Thr Val Glu Ala Ile  Asn Arg Glu Ala Val Asn His
  Gly Leu Arg Leu Ala Lys Gln Asp Ser Arg Ser His Lys Gln Arg Ser Ser Glu Ser Pro
GAGGCCTTCGCCTGGCTAAACAGGACAGTAGAAGCCATAAACAGAGAAGCAGTGAATCAC

Leu Pro Arg Glu Leu Ile  Phe Gln Val Trp Gln Arg Ser Trp Arg Tyr Trp His Asp Glu
  Thr Pro Arg Thr Tyr Phe Pro Gly Val Ala Glu Val Leu Glu Ile  Leu Ala
CTACCCCGAGAACTTATTTTCCAGGTGTGGCAGAGGTCCTGGAGATACTGGCATGATGAA
                                         5500

Gln Gly Met Ser Glu Ser Tyr Thr Lys Tyr Arg Tyr Leu Cys Ile  Ile  Gln Lys Ala Val
CAAGGGATGTCAGAAAGTTACACAAAGTATAGATATTTGTGCATAATACAGAAAGCAGTG

Tyr Met His Val Arg Lys Lys Cys Thr Cys Leu Gly Arg Gly His Gly Pro Gly Gly Trp
TACATGCATGTTAGGAAAGGGTGTACTTGCCTGGGGAGGGGACATGGGCCAGGAGGGTGG
                      5600

Arg Pro Gly Pro Pro Pro Pro Pro Pro Pro Gly Leu Val
                                                    Met Ala Glu Ala Pro Thr Glu
AGACCAGGGCCTCCTCCTCCTCCCCCTCCAGGTCTGGTCTAATGGCTGAAGCACCAACAG
                                                            5700

Leu Pro Pro Val Asp Gly Thr Pro Leu Arg Glu Pro Gly Asp Glu Trp Ile  Ile  Glu Ile
AGCTCCCCCCGGTGGATGGGACCCCACTGAGGGAGCCAGGGGATGAGTGGATAATAGAAA

Leu Arg Glu Ile  Lys Glu Glu Ala Leu Lys His Phe Asp Pro Arg Leu Leu Ile  Ala Leu
TCTTGAGAGAAATAAAAGAAGAAGCTTTAAAGCATTTTGACCCTCGCTTGCTAATTGCTC
                                         5800

Met Glu Thr Pro Leu Lys Ala Pro Glu Ser Ser Leu
    Gly Lys Tyr Ile  Tyr Thr Arg His Gly Asp Thr Leu Glu Gly Ala Arg Glu Leu Ile  Lys
TTGGCAAATATATCTATACTAGACATGGAGACACCCTTGAAGGCGCCAGAGAGCTCATTA

Lys Ser Cys Asn Glu Pro Phe Ser Arg Thr Ser Glu Gln Asp Val Ala Thr Gln Glu Leu
   Val Leu Gln Arg Ala Leu Phe Thr His Phe Arg Ala Gly Cys Gly His Ser Arg Ile  Gly
AAGTCCTGCAACGAGCCCTTTTCACGCACTTCAGAGCAGGATGTGGCCACTCAAGAATTG
                   5900

Ala Arg Gln Gly Glu Glu Ile  Leu Ser Gln Leu Tyr Arg Pro Leu Glu Thr Cys Asn Asn
   Gln Thr Arg Gly Gly Asn Pro Leu Ser Ala Ile  Pro Thr Pro Arg Asn Met Gln
GCCAGACAAGGGGAGGAAATCCTCTCTCAGCTATACCGACCCCTAGAAACATGCAATAAC
                                                            6000

Ser Cys Tyr Cys Lys Arg Cys Cys Tyr His Cys Gln Met Cys Phe Leu Asn Lys Gly Leu
TCATGCTATTGTAAGCCATGCTGCTACCATTGTCAGATGTGTTTTCTAAACAAGGGGCTC

Gly Ile  Cys Tyr Glu Arg Lys Gly Arg Arg Arg Thr Pro Lys Lys Thr Lys Thr His
           Met Asn Glu Arg Ala Asp Glu Glu Gly Leu Gln Arg Lys Leu Arg Leu Ile
GGGATATGTTATGAACGAAAGGGCAGACGAAGAAGGACTCCAAAGAAAACTAAGACTCAT
                                         6100
```

```
Pro Ser Pro Thr Pro Asp Lys
Arg Leu Leu His Gln Thr
                                  Met Met Asn Gln Leu Leu Ile  Ala Ile  Leu Leu Ala
CCGTCTCCTACACCAGACAAGTGAGTATGATGAATCAGCTGCTTATTGCCATTTTATTAG

Ser Ala Cys Leu Val Tyr Cys Thr Gln Tyr Val Thr Val Phe Tyr Gly Val Pro Thr Trp
CTAGTGCTTGCTTAGTATATTGCACCCAATATGTAACTGTTTTCTATGGCGTACCCACGT
                   6200

Lys Asn Ala Thr Ile  Pro Leu Phe Cys Ala Thr Arg Asn Arg Asp Thr Trp Gly Thr Ile
GGAAAAATGCAACCATTCCCCTCTTTTGTGCAACCAGAAATAGGGATACTTGGGGAACCA
                                                                    6300

Gln Cys Leu Pro Asp Asn Asp Asp Tyr Gln Glu Ile  Thr Leu Asn Val Thr Glu Ala Phe
TACAGTGCTTGCCTGACAATGATGATTATCAGGAAATAACTTTGAATGTAACAGAGGCTT

Asp Ala Trp Asn Asn Thr Val Thr Glu Gln Ala Ile  Glu Aso Val Trp His Leu Phe Glu
TTGATGCATGGAATAATACAGTAACAGAACAAGCAATAGAAGATGTCTGGCATCTATTCG
                                              6400

Thr Ser Ile  Lys Pro Cys Val Lys Leu Thr Pro Leu Cys Val Ala Met Lys Cys Ser Ser
AGACATCAATAAAACCATGTGTCAAACTAACACCTTTATGTGTAGCAATGAAATGCAGCA

Thr Glu Ser Ser Thr Gly Asn Asn Thr Thr Ser Lys Ser Thr Ser Thr Thr Thr Thr Thr
GCACAGAGAGCAGCACAGGGAACAACACAACCTCAAAGAGCACAAGCACAACCACAACCA
                  6500

Pro Thr Asp Gln Glu Gln Glu Ile  Ser Glu Asp Thr Pro Cys Ala Arg Ala Asp Asn Cys
CACCCACAGACCAGGAGCAAGAGATAAGTGAGGATACTCCATGCGCACGCGCAGACAACT
                                                                    6600

Ser Gly Leu Gly Glu Glu Glu Thr Ile  Asn Cys Gln Phe Asn Met Thr Gly Leu Glu Arg
GCTCAGGATTGGGAGAGGAAGAAACGATCAATTGCCAGTTCAATATGACAGGATTAGAAA

Asp Lys Lys Lys Gln Tyr Asn Glu Thr Trp Tyr Ser Lys Asp Val Val Cys Glu Thr Asn
GAGATAAGAAAAAACAGTATAATGAAACATGGTACTCAAAAGATGTGGTTTGTGAGACAA
                                       6700

Asn Ser Thr Asn Gln Thr Gln Cys Tyr Met Asn His Cys Asn Thr Ser Val Ile  Thr Glu
ATAATAGCACAAATCAGACCCAGTGTTACATGAACCATTGCAACACATCAGTCATCACAG

Ser Cys Asp Lys His Tyr Trp Asp Ala Ile  Arg Phe Arg Tyr Cys Ala Pro Pro Gly Tyr
AATCATGTGACAAGCACTATTGGGATGCTATAAGGTTTAGATACTGTGCACCACCGGGTT
                 6800

Ala Leu Leu Arg Cys Asn Asp Thr Asn Tyr Ser Gly Phe Ala Pro Asn Cys Ser Lys Val
ATGCCCTATTAAGATGTAATGATACCAATTATTCAGGCTTTGCACCCAACTGTTCTAAAG
                                                                    6900

Val Ala Ser Thr Cys Thr Arg Met Met Glu Thr Gln Thr Ser Thr Trp Phe Gly Phe Asn
TAGTAGCTTCTACATGCACCAGGATGATGGAAACGCAAACTTCCACATGGTTTGGCTTTA

Gly Thr Arg Ala Glu Asn Arg Thr Tyr Ile  Tyr Trp His Gly Arg Asp Asn Arg Thr Ile
ATGGCACTAGAGCAGAGAATAGAACATATATCTATTGGCATGGCAGAGATAATAGAACTA
                                              7000

Ile  Ser Leu Asn Lys Tyr Tyr Asn Leu Ser Leu His Cys Lys Arg Pro Gly Asn Lys Thr
TCATCAGCTTAAACAAATATTATAATCTCAGTTTGCATTGTAAGAGGCCAGGGAATAAGA

Val Lys Gln Ile  Met Leu Met Ser Gly His Val Phe His Ser His Tyr Gln Pro Ile  Asn
CAGTGAAACAAATAATGCTTATGTCAGGACATGTGTTTCACTCCCACTACCAGCCGATCA
                  7100

Lys Arg Pro Arg Gln Ala Trp Cys Trp Phe Lys Gly Lys Trp Lys Asp Ala Met Gln Glu
ATAAAAGACCCAGACAAGCATGGTGCTGGTTCAAAGGCAAATGGAAAGACGCCATGCAGG
                                                                    7200

Val Lys Glu Thr Leu Ala Lys His Pro Arg Tyr Arg Gly Thr Asn Asp Thr Arg Asn Ile
AGGTGAAGGAAACCCTTGCAAAACATCCCAGGTATAGAGGAACCAATGACACAAGGAATA

Ser Phe Ala Ala Pro Gly Lys Gly Ser Asp Pro Glu Val Ala Tyr Met Trp Thr Asn Cys
TTAGCTTTGCAGCGCCAGGAAAAGGCTCAGACCCAGAAGTAGCATACATGTGGACTAACT
                                     7300
```

-continued

Arg Gly Glu Phe Leu Tyr Cys Asn Met Thr Trp Phe Leu Asn Trp Ile Glu Asn Lys Thr
GCAGAGGAGAGTTTCTCTACTGCAACATGACTTGGTTCCTCAATTGGATAGAGAATAAGA

His Arg Asn Tyr Ala Pro Cys His Ile Lys Gln Ile Ile Asn Thr Trp His Lys Val Gly
CACACCGCAATTATGCACCGTGCCATATAAAGCAAATAATTAACACATGGCATAAGGTAG
                       7400

Arg Asn Val Tyr Leu Pro Pro Arg Glu Gly Glu Leu Ser Cys Asn Ser Thr Val Thr Ser
GGAGAAATGTATATTTGCCTCCCAGGGAAGGGGAGCTGTCCTGCAACTCAACAGTAACCA
                                            7500

Ile Ile Ala Asn Ile Asp Trp Gln Asn Asn Asn Gln Thr Asn Ile Thr Phe Ser Ala Glu
GCATAATTGCTAACATTGACTGGCAAAACAATAATCAGACAAACATTACCTTTAGTGCAG

Val Ala Glu Leu Tyr Arg Leu Glu Leu Gly Asp Tyr Lys Leu Val Glu Ile Thr Pro Ile
AGGTGGCAGAACTATACAGATTGGAGTTGGGAGATTATAAATTGGTAGAAATAACACCAA
                            7600

Gly Phe Ala Pro Thr Lys Glu Lys Arg Tyr Ser Ser Ala His Gly Arg His Thr Arg Gly
TTGGCTTCGCACCTACAAAAGAAAAAAGATACTCCTCTGCTCACGGGAGACATACAAGAG

Val Phe Val Leu Gly Phe Leu Gly Phe Leu Ala Thr Ala Gly Ser Ala Met Gly Ala Ala
GTGTGTTCGTGCTAGGGTTCTTGGGTTTTCTCGCAACAGCAGGTTCTGCAATGGGCGCGG
                 7700

Ser Leu Thr Val Ser Ala Gln Ser Arg Thr Leu Leu Ala Gly Ile Val Gln Gln Gln Gln
CGTCCCTGACCGTGTCGGCTCAGTCCCGGACTTTACTGGCCGGGATAGTGCAGCAACAGC
                                          7800

Gln Leu Leu Asp Val Val Lys Arg Gln Gln Glu Leu Leu Arg Leu Thr Val Trp Gly Thr
AACAGCTGTTGGACGTGGTCAAGAGACAACAAGAACTGTTGCGACTGACCGTCTGGGGAA

Lys Asn Leu Gln Ala Arg Val Thr Ala Ile Glu Lys Tyr Leu Gln Asp Gln Ala Arg Leu
CGAAAAACCTCCAGGCAACAGTCACTGCTATAGAGAAGTACCTACAGGACCAGGCGCGGC
                               7900

Asn Ser Trp Gly Cys Ala Phe Arg Gln Val Cys His Thr Thr Val Pro Trp Val Asn Asp
TAAATTCATGGGGATGTGCGTTTAGACAAGTCTGCCACACTACTGTACCATGGGTTAATG

Ser Leu Ala Pro Asp Trp Asp Asn Met Thr Trp Gln Glu Trp Glu Lys Gln Val Arg Tyr
ATTCCTTAGCACCTGACTGGGACAATATGACGTGGCAGGAATGGGAAAAACAAGTCCGCT
                 8000

Leu Glu Ala Asn Ile Ser Lys Ser Leu Glu Gln Ala Gln Ile Gln Gln Glu Lys Asn Met
ACCTGGAGGCAAATATCAGTAAAAGTTTAGAACAGGCACAAATTCAGCAAGAGAAAAATA
                                          8100

Tyr Glu Leu Gln Lys Leu Asn Ser Trp Asp Ile Phe Gly Asn Trp Phe Asp Leu Thr Ser
TGTATGAACTACAAAAATTAAATAGCTGGGATATTTTTGGCAATTGGTTTGACTTAACCT

Trp Val Lys Tyr Ile Gln Tyr Gly Val Leu Ile Ile Val Ala Val Ile Ala Leu Arg Ile
CCTGGGTCAAGTATATTCAATATGGAGTGCTTATAATAGTAGCAGTAATAGCTTTAAGAA
                                   8200

Val Ile Tyr Val Val Gln Met Leu Ser Arg Leu Arg Lys Gly Tyr Arg Pro Val Phe Ser
TAGTGATATATGTAGTACAAATGTTAAGTAGGCTTAGAAAGGGCTATAGGCCTGTTTTCT

Ser Ile Ser Thr Arg Thr Gly Asp Ser Gln Pro
                           Asn Pro Tyr Pro Gln Gly Pro Gly Thr Ala Ser Gln
Ser Pro Pro Gly Tyr Ile Gln Gln Ile His Ile His Lys Asp Arg Gly Gln Pro Ala Asn
CTTCCCCCCCCGGTTATATCCAACAGATCCATATCCACAAGGACCGGGGACAGCCAGCCA
                 8300

Thr Lys Lys Gln Lys Lys Thr Val Glu Ala Thr Val Glu Thr Asp Thr Gly Pro Gly Arg
Arg Arg Asn Arg Arg Arg Arg Trp Lys Gln Arg Trp Arg Gln Ile Leu Ala Leu Ala Asp
Glu Glu Thr Glu Glu Asp Gly Gly Ser Asn Gly Gly Asp Arg Tyr Trp Pro Trp Pro Ile
ACGAAGAAACAGAAGAAGACGGTGGAAGCAACGGTGGAGACAGATACTGGCCCTGGCCGA
                                            8400

Ser Ile Tyr Thr Phe Pro Asp Pro Pro Ala Asp Ser Pro Leu Asp Gln Thr Ile Gln His
Ala Tyr Ile His Phe Leu Ile Arg Gln Leu Ile Arg Leu Leu Thr Arg Leu Tyr Ser Ile
TAGCATATATACATTTCCTGATCCGCCAGCTGATTCGCCTCTTGACCAGACTATACAGCA

-continued

```
Leu Gln Gly Leu Thr Ile  Gln Glu Leu Pro Asp Pro Pro Thr His Leu Pro Glu Ser Gln
   Cys Arg Asp Leu Leu Ser Arg Ser Phe Leu Thr Leu Gln Leu Ile  Tyr Gln Asn Leu Arg
TCTGCAGGGACTTACTATCCAGGAGCTTCCTGACCCTCCAACTCATCTACCAGAATCTCA
                                        8500

Arg Leu Ala Glu Thr                                Met Gly Ala Ser Gly Ser Lys Lys
   Asp Trp Leu Arg Leu Arg Thr Ala Phe Leu Gln Tyr Gly Cys Glu Trp Ile  Gln Glu Ala
GAGACTGGCTGAGACTTAGAACAGCCTTCTTGCAATATGGGTGCGAGTGGATCCAAGAAG

His Ser Arg Pro Pro Arg Gly Leu Gln Glu Arg Leu Leu Arg Ala Arg Ala Gly Ala Cys
   Phe Gln Ala Ala Ala Arg Ala Thr Arg Glu Thr Leu Ala Gly Ala Cys Arg Gly Leu Trp
CATTCCAGGCCGCCGCGAGGGCTACAAGAGAGACTCTTGCGGGCGCGTGCAGGGGCTTGT
                        8600

Gly Gly Tyr Trp Asn Glu Ser Gly Gly Glu Tyr Ser Arg Phe Gln Glu Gly Ser Asp Arg
   Arg Val Leu Glu Arg Ile  Gly Arg Gly Ile  Leu Ala Val Pro Arg Arg Ile  Arg Gln Gly
GGAGGGTATTGGAACGAATCGGGAGGGGAATACTCGCGGTTCCAAGAAGGATCAGACAGG
                                                                  8700

Glu Gln Lys Ser Pro Ser Cys Glu Gly Arg Gln Tyr Gln Gln Gly Asp Phe Met Asn Thr
   Ala Glu Ile  Ala Leu Leu
GAGCAGAAATCGCCCTCCTGTGAGGGACGGCAGTATCAGCAGGGAGACTTTATGAATACT

Pro Trp Lys Asp Pro Ala Ala Glu Arg Glu Lys Asn Leu Tyr Arg Gln Gln Asn Met Asp
CCATGGAAGGACCCAGCAGCAGAAAGGGAGAAAAATTTGTACAGGCAACAAAATATGGAT
                                        8800

Asp Val Asp Ser Asp Asp Asp Asp Gln Val Arg Val Ser Val Thr Pro Lys Val Pro Leu
GATGTAGATTCAGATGATGATGACCAAGTAAGAGTTTCTGTCACACCAAAAGTACCACTA

Arg Pro Met Thr His Arg Leu Ala Ile  Asp Met Ser His Leu Ile  Lys Thr Arg Gly Gly
AGACCAATGACACATAGATTGGCAATAGATATGTCACATTTAATAAAAACAAGGGGGGGA
                        8900

Leu Glu Gly Met Phe Tyr Ser Glu Arg Arg His Lys Ile  Leu Asn Ile  Tyr Leu Glu Lys
CTGGAAGGGATGTTTTACAGTGAAAGAAGACATAAAATCTTAAATATATACTTAGAAAAG
                                                                  9000

Glu Glu Gly Ile  Ile  Ala Asp Trp Gln Asn Tyr Thr His Gly Pro Gly Val Arg Tyr Pro
GAAGAAGGGATAATTGCAGATTGGCAGAACTACACTCATGGGCCAGGAGTAAGATACCCA

Met Phe Phe Gly Trp Leu Trp Lys Leu Val Pro Val Asp Val Pro Gln Glu Gly Glu Asp
ATGTTCTTTGGGTGGCTATGGAAGCTAGTACCAGTAGATGTCCCACAAGAAGGGGAGGAC
                                        9100

Thr Glu Thr His Cys Leu Val His Pro Ala Gln Thr Ser Lys Phe Asp Asp Pro His Gly
ACTGAGACTCACTGCTTAGTACATCCAGCACAAACAAGCAAGTTTGATGACCCGCATGGG

Glu Thr Leu Val Trp Glu Phe Asp Pro Leu Leu Ala Tyr Ser Tyr Glu Ala Phe Ile  Arg
GAGACACTAGTCTGGGAGTTTGATCCCTTGCTGGCTTATAGTTACGAGGCTTTTATTCGG
                        9200

Tyr Pro Glu Glu Phe Gly His Lys Ser Gly Leu Pro Glu Glu Glu Trp Lys Ala Arg Leu
TACCCAGAGGAATTTGGGCACAAGTCAGGCCTGCCAGAGGAAGAGTGGAAGGCGAGACTG
                                                                  9300

Lys Ala Arg Gly Ile  Pro Phe Ser
AAAGCAAGAGGAATACCATTTAGTTAAAGACAGGAACAGCTATACTTGGTCAGGGCAGGA

AGTAACTAACAGAAACAGCTGAGACTGCAGGGACTTTCCAGAAGGGGCTGTAACCAAGGG
                                        9400

AGGGACATGGGAGGAGCTGGTGGGGAACGCCCTCATATTCTCTGTATAAATATACCCGCT

AGCTTGCATTGTACTTCGGTCGCTCTGCGGAGAGGCTGGCAGATTGAGCCCTGGGAGGTT
                        9500

CTCTCCAGCAGTAGCAGGTAGAGCCTGGGTGTTCCCTGCTAGACTCTCACCAGCACTTGG
                                                                  9600

CCGGTGCTGGGCAGACGGCCCCACGCTTGCTTGCTTAAAAACCTCCTTAATAAAGCTGCC

AGTTAGAAGCA
```

Example 5

Sequences of the Coding Regions for the Envelope Protein and GAG Product of the ROD HIV-2 Isolate Through experimental analysis of the HIV-2 ROD isolate, the following sequences were identified for the regions encoding the env and gag gene products. One of ordinary skill in the art will recognize that the numbering for both gene regions which follow begins for convenience with "1" rather than the corresponding number for its initial nucleotide as given in Example 4, above, in the context of the complete genomic sequence.

Envelope sequence

```
Met Met Asn Gln Leu Leu Ile  Ala Ile  Leu Leu Ala Ser Ala Cys
ATGATGAATCAGCTGCTTATTGCCATTTTATTAGCTAGTGCTTGC

Leu Val Tyr Cys Thr Gln Tyr Val Thr Val Phe Tyr Gly Val Pro
TTAGTATATTGCACCCAATATGTAACTGTTTTCTATGGCGTACCC

Thr Trp Lys Asn Ala Thr Ile  Pro Leu Phe Cys Ala Thr Arg Asn
ACGTGGAAAAATGCAACCATTCCCCTCTTTTGTGCAACCAGAAAT
                  100

Arg Asp Thr Trp Gly Thr Ile  Gln Cys Leu Pro Asp Asn Asp Asp
AGGGATACTTGGGGAACCATACAGTGCTTGCCTGACAATGATGAT

Tyr Gln Glu Ile  Thr Leu Asn Val Thr Glu Ala Phe Asp Ala Trp
TATCAGGAAATAACTTTGAATGTAACAGAGGCTTTTGATGCATGG
                        200

Asn Asn Thr Val Thr Glu Gln Ala Ile  Glu Asp Val Trp His Leu
AATAATACAGTAACAGAACAAGCAATAGAAGATGTCTGGCATCTA

Phe Glu Thr Ser Ile  Lys Pro Cys Val Lys Leu Thr Pro Leu Cys
TTCGAGACATCAATAAAACCATGTGTGAAACTAACACCTTTATGT
                              300

Val Ala Met Lys Cys Ser Ser Thr Glu Ser Ser Thr Gly Asn Asn
GTAGCAATGAAATGCAGCAGCACAGAGAGCAGCACAGGGAACAAC

Thr Thr Ser Lys Ser Thr Ser Thr Thr Thr Thr Thr Pro Thr Asp
ACAACCTCAAAGAGCACAAGCACAACCACAACCACACCCAGAGAC
                                      400

Gln Glu Gln Glu Ile  Ser Glu Asp Thr Pro Cys Ala Arg Ala Asp
CAGGAGCAAGAGATAAGTGAGGATACTCCATGCGCACGCGCAGAC

Asn Cys Ser Gly Leu Gly Glu Glu Glu Thr Ile  Asn Cys Gln Phe
AACTGCTCAGGATTGGGAGAGGAAGAAACGATCAATTGCCAGTTC

Asn Met Thr Gly Leu Glu Arg Asp Lys Lys Lys Gln Tyr Asn Glu
AATATGACAGGATTAGAAAGAGATAAGAAAAAACAGTATAATGAA
    500

Thr Trp Tyr Ser Lys Asp Val Val Cys Glu Thr Asn Asn Ser Thr
ACATGGTACTCAAAAGATGTGGTTTGTGAGACAAATAATAGCACA

Asn Gln Thr Gln Cys Tyr Met Asn His Cys Asn Thr Ser Val Ile
AATCAGACCCAGTGTTACATGAACCATTGCAACACATCAGTCATC
                      600

Thr Glu Ser Cys Asp Lys His Tyr Trp Asp Ala Ile  Arg Phe Arg
ACAGAATCATGTGACAAGCACTATTGGGATGCTATAAGGTTTAGA

Tyr Cys Ala Pro Pro Gly Tyr Ala Leu Leu Arg Cys Asn Asp Thr
TACTGTGCACCACCGGGTTATGCCCTATTAAGATGTAATGATACC
                      700

Asn Tyr Ser Gly Phe Ala Pro Asn Cys Ser Lys Val Val Ala Ser
AATTATTCAGGCTTTGCACCCAACTGTTCTAAAGTAGTAGCTTCT
```

-continued

Thr Cys Thr Arg Met Met Glu Thr Gln Thr Ser Thr Trp Phe Gly
ACATGCACCAGGATGATGGAAACGCAAACTTCCACATGGTTTGGC
                                800

Phe Asn Gly Thr Arg Ala Glu Asn Arg Thr Tyr Ile Tyr Trp His
TTTAATGGCACTAGAGCAGAGAATAGAACATATATCTATTGGCAT

Gly Arg Asp Asn Arg Thr Ile Ile Ser Leu Asn Lys Tyr Tyr Asn
GGCAGAGATAATAGAACTATCATCAGCTTAAACAAATATTATAAT
                                                900

Leu Ser Leu His Cys Lys Arg Pro Gly Asn Lys Thr Val Lys Gln
CTCAGTTTGCATTGTAAGAGGCCAGGGAATAAGACAGTGAAACAA

Ile Met Leu Met Ser Gly His Val Phe His Ser His Tyr Gln Pro
ATAATGCTTATGTCAGGACATGTGTTTCACTCCCACTACCAGCCG
       ↓
Ile Asn Lys Arg Pro Arg Gln Ala Trp Cys Trp Phe Lys Gly Lys
ATCAATAAAAGACCCAGACAAGCATGGTGCTGGTTCAAAGGCAAA
            1000
              ↓
Trp Lys Asp Ala Met Gln Glu Val Lys Thr Leu Ala Lys His Pro
TGGAAAGACGCCATGCAGGAGGTGAAGACCCTTGCAAAACATCCC

Arg Tyr Arg Gly Thr Asn Asp Thr Arg Asn Ile Ser Phe Ala Ala
AGGTATAGAGGAACCAATGACACAAGGAATATTAGCTTTGCAGCG
                    1100

Pro Gly Lys Gly Ser Asp Pro Glu Val Ala Tyr Met Trp Thr Asn
CCAGGAAAAGGCTCAGACCCAGAAGTAGCATACATGTGGACTAAC

Cys Arg Gly Glu Phe Leu Tyr Cys Asn Met Thr Trp Phe Leu Asn
TGCAGAGGAGAGTTTCTCTACTGCAACATGACTTGGTTCCTCAAT
                              1200

Trp Ile Glu Asn Lys Thr His Arg Asn Tyr Ala Pro Cys His Ile
TGGATAGAGAATAAGACACACCGCAATTATGCACCGTGCCATATA

Lys Gly Ile Ile Asn Thr Trp His Lys Val Gly Arg Asn Val Tyr
AAGCAAATAATTAACACATGGCATAAGGTAGGGAGAAATGTATAT
                                          1300

Leu Pro Pro Arg Glu Gly Glu Leu Ser Cys Asn Ser Thr Val Thr
TTGCCTCCCAGGGAAGGGGAGCTGTCCTGCAACTCAACAGTAACC

Ser Ile Ile Ala Asn Ile Asp Trp Gln Asn Asn Gln Thr Asn
AGCATAATTGCTAACATTGACTGGCAAAACAATAATCAGACAAAC

Ile Thr Phe Ser Ala Glu Val Ala Glu Leu Tyr Arg Leu Glu Leu
ATTACCTTTAGTGCAGAGGTGGCAGAACTATACAGATTGGAGTTG
    1400

Gly Asp Tyr Lys Leu Val Glu Ile Thr Pro Ile Gly Phe Ala Pro
GGAGATTATAAATTGGTAGAAATAACACCAATTGGCTTCGCACCT

Thr Lys Glu Lys Arg Tyr Ser Ser Ala His Gly Arg His Thr Arg
ACAAAAGAAAAAAGATACTCCTCTGCTCACGGGAGACATACAAGA
                1500

Gly Val Phe Val Leu Gly Phe Leu Gly Phe Leu Ala Thr Ala Gly
GGTGTGTTCGTGCTAGGGTTCTTGGGTTTTCTCGCAACAGCAGGT

Ser Ala Met Gly Ala Arg Ala Ser Leu Thr Val Ser Ala Gln Ser
TCTGCAATGGGCGCTCGAGCGTCCCTGACCGTGTCGGCTCAGTCC
                          1600

Arg Thr Leu Leu Ala Gly Ile Val Gln Gln Gln Gln Gln Leu Leu
CGGACTTTACTGGCCGGGATAGTGCAGCAACAGCAACAGCTGTTG

Asp Val Val Lys Arg Gln Gln Glu Leu Leu Arg Leu Thr Val Trp
GACGTGGTCAAGAGACAACAAGAACTGTTGCGACTGACCGTCTGG
                                        1700

-continued

```
Gly Thr Lys Asn Leu Gln Ala Arg Val Thr Ala Ile  Glu Lys Tyr
GGAACGAAAAACCTCCAGGCAAGAGTCACTGCTATAGAGAAGTAG

Leu Gln Asp Gln Ala Arg Leu Asn Ser Trp Gly Cys Ala Phe Arg
CTACAGGACCAGGCGCGGCTAAATTCATGGGGATGTGCGTTTAGA
                                                    1800

Gln Val Cys His Thr Thr Val Pro Trp Val Asn Asp Ser Leu Ala
CAAGTCTGCCACACTACTGTACCATGGGTTAATGATTCCTTAGCA

Pro Asp Trp Asp Asn Met Thr Trp Gln Glu Trp Glu Lys Gln Val
CCTGACTGGGACAATATGACGTGGCAGGAATGGGAAAAACAAGTC

Arg Tyr Leu Glu Ala Asn Ile  Ser Lys Ser Leu Glu Gln Ala Gln
CGCTACCTGGAGGCAAATATCAGTAAAAGTTTAGAACAGGCACAA
            1900

Ile  Gln Gln Glu Lys Asn Met Tyr Glu Leu Gln Lys Leu Asn Ser
ATTCAGCAAGAGAAAAATATGTATGAACTACAAAAATTAAATAGC

Trp Asp Ile  Phe Gly Asn Trp Phe Asp Leu Thr Ser Trp Val Lys
TGGGATATTTTTGGCAATTGGTTTGACTTAACCTCCTGGGTCAAG
                    2000

Tyr Ile  Gln Tyr Gly Val Leu Ile  Ile  Val Ala Val Ile  Ala Leu
TATATTCAATATGGAGTGCTTATAATAGTAGCAGTAATAGCTTTA

Arg Ile  Val Ile  Tyr Val Val Gln Met Leu Ser Arg Leu Arg Lys
AGAATAGTGATATATGTAGTACAAATGTTAAGTAGGCTTAGAAAG
                            2100

Gly Tyr Arg Pro Val Phe Ser Ser Pro Pro Gly Tyr Ile  Gln ***
GGCTATAGGCCTGTTTTCTCTTCCCCCCCCGGTTATATCCAATAG

Ile  His Ile  His Lys Asp Arg Gly Gln Pro Ala Asn Glu Glu Thr
ATCCATATCCACAAGGACCGGGGACAGCCAGCCAACGAAGAAACA
                                                    2200

Glu Glu Asp Gly Gly Ser Asn Gly Gly Asp Arg Tyr Trp Pro Trp
GAAGAAGACGGTGGAAGCAACGGTGGAGACAGATACTGGCCCTGG

Pro Ile  Ala Tyr Ile  His Phe Leu Ile  Arg Gln Leu Ile  Arg Leu
CCGATAGCATATATACATTTCCTGATCCGCCAGCTGATTCGCCTC

Leu Thr Arg Leu Tyr Ser Ile  Cys Arg Asp Leu Leu Ser Arg Ser
TTGACCAGACTATACAGCATCTGCAGGGACTTACTATCCAGGAGC
    2300

Phe Leu Thr Leu Gln Leu Ile  Tyr Gln Asn Leu Arg Asp Trp Leu
TTCCTGACCCTCCAACTCATCTACCAGAATCTCAGAGACTGGCTG

Arg Leu Arg Thr Ala Phe Leu Gln Tyr Gly Cys Glu Trp Ile  Gln
AGACTTAGAACAGCCTTCTTGCAATATGGGTGCGAGTGGATCCAA
            2400

Glu Ala Phe Gln Ala Ala Ala Arg Ala Thr Arg Glu Thr Leu Ala
GAAGCATTCCAGGCCGCCGCGAGGGCTACAAGAGAGACTCTTGCG

Gly Ala Cys Arg Gly Leu Trp Arg Val Leu Glu Arg Ile  Gly Arg
GGCGCGTGCAGGGGCTTGTGGAGGGTATTGGAACGAATCGGGAGG
                    2500

Gly Ile  Leu Ala Val Pro Arg Arg Ile  Arg Gln Gly Ala Glu Ile
GGAATACTCGCGGTTCCAAGAAGGATCAGACAGGGAGCAGAAATC

Ala Leu Leu *** Gly Thr Ala Val Ser Ala Gly Arg Leu Tyr Glu
GCCCTCCTGTGAGGGACGGCAGTATCAGCAGGGAGACTTTATGAA
                            2600

Tyr Ser Met Glu Gly Pro Ser Ser Arg Lys Gly Glu Lys Phe Val
TACTCCATGGAAGGACCCAGCAGCAGAAAGGGAGAAAAATTTGTA
```

Gln Ala Thr Lys Tyr Gly
CAGGCAACAAAATATGGA

Gag sequence

Met Gly Ala Arg Asn Ser Val Leu Arg Gly Lys Lys Ala Asp Glu
ATGGGCGCGAGAAACTCCGTCTTGAGAGGGAAAAAAGCAGATGAA

Leu Glu Arg Ile Arg Leu Arg Pro Gly Gly Lys Lys Lys Tyr Arg
TTAGAAAGAATCAGGTTACGGCCCGGCGGAAAGAAAAAGTACAGG

Leu Lys His Ile Val Trp Ala Ala Asn Lys Leu Asp Arg Phe Gly
CTAAAACATATTGTGTGGGCAGCGAATAAATTGGACAGATTCGGA
                100

Leu Ala Glu Ser Leu Leu Glu Ser Lys Glu Gly Cys Gln Lys Ile
TTAGCAGAGAGCCTGTTGGAGTCAAAAGAGGGTTGTCAAAAAATT

Leu Thr Val Leu Asp Pro Met Val Pro Thr Gly Ser Glu Asn Leu
CTTACAGTTTTAGATCCAATGGTACCGACAGGTTCAGAAAATTTA
                   200

Lys Ser Leu Phe Asn Thr Val Cys Val Ile Trp Cys Ile His Ala
AAAAGTCTTTTTAATACTGTCTGCGTCATTTGGTGCATACACGCA

Glu Glu Lys Val Lys Asp Thr Glu Gly Ala Lys Gln Ile Val Arg
GAAGAGAAAGTGAAAGATACTGAAGGAGCAAAACAAATAGTGCGG
                              300

Arg His Leu Val Ala Glu Thr Gly Thr Ala Glu Lys Met Pro Ser
AGACATCTAGTGGCAGAAACAGGAACTGCAGAGAAAATGCCAAGC

Thr Ser Arg Pro Thr Ala Pro Ser Ser Glu Lys Gly Gly Asn Tyr
ACAAGTAGACCAACAGCACCATCTAGCGAGAAGGGAGGAAATTAC
                                    400

Pro Val Gln His Val Gly Gly Asn Tyr Thr His Ile Pro Leu Ser
CCAGTGCAACATGTAGGCGGCAACTACACCCATATACCGCTGAGT

Pro Arg Thr Leu Asn Ala Trp Val Lys Leu Val Glu Glu Lys Lys
CCCCGAACCCTAAATGCCTGGGTAAAATTAGTAGAGGAAAAAAAG

Phe Gly Ala Glu Val Val Pro Gly Phe Gln Ala Leu Ser Glu Gly
TTCGGGGCAGAAGTAGTGCCAGGATTTCAGGCACTCTCAGAAGGC
   500

Cys Thr Pro Tyr Asp Ile Asn Gln Met Leu Asn Cys Val Gly Asp
TGCACGCCCTATGATATCAACCAAATGCTTAATTGTGTGGGCGAC

His Gln Ala Ala Met Gln Ile Ile Arg Glu Ile Ile Asn Glu Glu
CATCAAGCAGCCATGCAGATAATCAGGGAGATTATCAATGAGGAA
                 600

Ala Ala Glu Trp Asp Val Gln His Pro Ile Pro Gly Pro Leu Pro
GCAGCAGAATGGGATGTGCAACATCCAATACCAGGCCCCTTACCA

Ala Gly Glu Leu Arg Glu Pro Arg Gly Ser Asp Ile Ala Gly Thr
GCGGGGCAGCTTAGAGAGCCAAGGGGATCTGACATAGCAGGGACA
                         700

Thr Ser Thr Val Glu Glu Gln Ile Gln Trp Met Phe Arg Pro Gln
ACAAGCACAGTAGAAGAACAGATCCAGTGGATGTTTAGGCCACAA

Asn Pro Val Pro Val Gly Asn Ile Tyr Arg Arg Trp Ile Gln Ile
AATCCTGTACCAGTAGGAAACATCTATAGAAGATGGATCCAGATA
                                 800

Gly Leu Gln Lys Cys Val Arg Met Tyr Asn Pro Thr Asn Ile Leu
GGATTGCAGAAGTGTGTCAGGATGTACAACCCGACCAACATCCTA

-continued

```
Asp Ile Lys Gln Gly Pro Lys Glu Pro Phe Gln Ser Tyr Val Asp
GACATAAAACAGGGACCAAAGGAGCCGTTCCAAAGCTATGTAGAT
                                                              900

Arg Phe Tyr Lys Ser Leu Arg Ala Glu Gln Thr Asp Pro Ala Val
AGATTCTACAAAAGCTTGAGGGCAGAACAAACAGATCCAGCAGTG

Lys Asn Trp Met Thr Gln Thr Leu Leu Val Gln Asn Ala Asn Pro
AAGAATTGGATGACCCAAACACTGCTAGTACAAAATGCCAACCCA

Asp Cys Lys Leu Val Leu Lys Gly Leu Gly Met Asn Pro Thr Leu
GACTGTAAATTAGTGCTAAAAGGACTAGGGATGAACCCTACCTTA
         1000

Glu Glu Met Leu Thr Ala Cys Gln Gly Val Gly Gly Pro Gly Gln
GAAGAGATGCTGACCGCCTGTCAGGGGGTAGGTGGGCCAGGCCAG

Lys Ala Arg Leu Met Ala Glu Ala Leu Lys Glu Val Ile Gly Pro
AAAGCTAGATTAATGGCAGAGGCCCTGAAAGAGGTCATAGGACCT
                    1100

Ala Pro Ile Pro Phe Ala Ala Ala Gln Gln Arg Lys Ala Phe Lys
GCCCCTATCCCATTCGCAGCAGCCCAGCAGAGAAAGGCATTTAAA

Cys Trp Asn Cys Gly Lys Glu Gly His Ser Ala Arg Gln Cys Arg
TGCTGGAACTGTGGAAAGGAAGGGCACTCGGCAAGACAATGCCGA
                            1200

Ala Pro Arg Arg Gln Gly Cys Trp Lys Cys Gly Lys Pro Gly His
GCACCTAGAAGGCAGGGCTGCTGGAAGTGTGGTAAGCCAGGACAC

Ile Met Thr Asn Cys Pro Asp Arg Gln Ala Gly Phe Leu Gly Leu
ATCATGACAAACTGCCCAGATAGACAGGCAGGTTTTTTAGGACTG
                                            1300

Gly Pro Trp Gly Lys Lys Pro Arg Asn Phe Pro Val Ala Gln Val
GGCCCTTGGGGAAAGAAGCCCCGCAACTTCCCCGTGGCCCAAGTT

Pro Gln Gly Leu Thr Pro Thr Ala Pro Pro Val Asp Pro Ala Val
CCGCAGGGGCTGACACCAACAGCACCCCCAGTGGATCCAGCAGTG

Asp Leu Leu Glu Lys Tyr Met Gln Gln Gly Lys Arg Gln Arg Glu
GATCTACTGGAGAAATATATGCAGCAAGGGAAAAGACAGAGAGAG
      1400

Gln Arg Glu Arg Pro Tyr Lys Glu Val Thr Glu Asp Leu Leu His
CAGAGAGAGAGACCATACAAGGAAGTGACAGAGGACTTACTGCAC

Leu Glu Gln Gly Glu Thr Pro Tyr Arg Glu Pro Pro Thr Glu Asp
CTCGAGCAGGGGGAGACACCATACAGGGAGCCACCAACAGAGGAC
               1500

Leu Leu His Leu Asn Ser Leu Phe Gly Lys Asp Gln
TTGCTGCACCTCAATTCTCTCTTTGGAAAAGACCAG
```

Example 6

Peptide Sequences Encoded By The ENV and GAG genes

The following coding regions for antigenic peptides, identified for convenience only by the nucleotide numbers of Example 5, within the env and gag gene regions are of particular interest.

env1 (1732–1809)

```
          Arg Tal Thr Ala Ile Glu Lys Tyr
          AGAGTCACTGCTATAGAGAAGTAC
```

-continued

```
                Leu Glu Asp Gln Ala Arg Leu Asn Ser Trp Gly Cys Ala Phe Arg
                CTACAGGACCAGGCGCGCCTAAATTCATGGGGATGTGCGTTTAGA
                                    .           .           .           1000
Gln Val Cys
CAAGTCTGC env2 (1912-1983)
                                Ser Lys Ser Leu Glu Gln Ala Gln
                                AGTAAAAGTTTAGAACAGGCACAA Ile Gln Gln Glu Lys Asn Met Tyr Glu Leu Gln Lys Leu Asn Ser
ATTCAGCAAGAGAAAAATATGTATGAACTACAAAAATTAAATAGC
 1940                .           .           .
Trp
TGG env3 (1482-1530)

Pro Thr Lys Glu Lys Arg Tyr Ser Ser Ala His Gly Arg His Thr Arg
CCTACAAAAGAAAAAAGATACTCCTCTGCTCACGGGAGACATACAAGA
             .          1500            .           .           .

env4 (55-129)

Cys Thr Gln Tyr Val Thr Val Phe Tyr Gly Val Pro
            TGCACCCAATATGTAACTGTTTTCTATGGCGTACCC

Thr Trp Lys Asn Ala Thr Ile Pro Leu Phe Cys Ala Thr
ACGTGGAAAAATGCAACCATTCCCCTGTTTTGTGCAACC
            100            .            .

env5 (175-231)
                                                Asp Asp
                                                GATGAT Tyr Glu Glu Ile Thr Leu Asn Val Thr Glu Ala Phe Asp Ala Trp
TATCAGGAAATAACTTTGAATGTAACAGAGGCTTTTGATGCATGG
             .          200            .           .
Asn Asn
AATAAT env6 (274-330)

Glu Thr Ser Ile Lys Pro Cys Val Lys Leu Thr Pro Leu Cys
    GAGACATCAATAAAACCATGTGTGAAACTAACACCTTTATGT
                        .           300            .
Val Ala Met Lys Cys
GTAGCAATGAAATGC
            .           .

env7 (607-660)

Asn His Cys Asn Thr Ser Val Ile
                                AACCATTGCAACACATCAGTCATC
                                            610            .           .
Thr Glu Ser Cys Asp Lys His Tyr Trp Asp
ACAGAATCATGTGACAAGCAGTATTGGGAT
            .           .           .

env8 (661-720)

Ala Ile Arg Phe Arg
                                    GCTATAAGGTTTAGA

Tyr Cys Ala Pro Pro Gly Tyr Ala Leu Leu Arg Cys Asn Asp Thr
TACTGTGCACCACCGGGTTATGCCCTATTAAGATGTAATGATACC
                        .           700            .           .

env9 (997-1044)

Lys Arg Pro Arg Gln Ala Trp Cys Trp Phe Lys Gly Lys
        AAAAGACCCAGACAAGCATGGTGCTGGTTGAAAGGCAAA
            1000            .           .           .
Trp Lys Asp
TGGAAAGAC env10 (1132-1215)

Lys Gly Ser Asp Pro Glu Val Ala Tyr Met Trp Thr Asn
        AAAGGCTCAGACCCAGAAGTAGCATACATGTGGACTAAC

Cys Arg Gly Glu Phe Leu Tyr Cys Asn Met Thr Trp Phe Leu Asn
TGCAGAGGAGAGTTTCTCTACTGCAACATGACTTGGTTCCTCAAT
            .           .          1200            .
```

-continued env11 (1237-1305)

```
                                Arg Asn Tyr Ala Pro Cys His Ile
                                CGCAATTATGCACCGTGCCATATA
Lys Gln Ile Ile Asn Thr Trp His Lys Val Gly Arg Asn Val Tyr
AAGCAAATAATTAACACATGGCATAAGGTAGGGAGAAATGTATAT
                                                1300
``` gag1 (991-1053)

```
Asp Cys Lys Leu Val Leu Lys Gly Leu Gly Met Asn Pro Thr Leu
GACTGTAAATTAGTGCTAAAAGGACTAGGGATGAACCCTACCTTA
      1000
Glu Glu Met Leu Thr Ala
GAAGAGATGCTGACCGCC
```

Of the foregoing peptides, env1, env2, env3 and gag1 are particularly contemplated for diagnostic purposes, and env4, env5, env6, env7, env8, env9, env10 and env11 are particularly contemplated as protecting agents. These peptides have been selected in part because of their sequence homology to certain of the envelope and gag protein products of other of the retroviruses in the HIV group. For vaccinating purposes, the foregoing peptides may be coupled to a carrier protein by utilizing suitable and well known techniques to enhance the host's immune response. Adjuvants such as calcium phosphate or alum hydroxide may also be added. The foregoing peptides can be synthesized by conventional protein synthesis techniques, such as that of Merrifield.

It will be apparent to those skilled in the art that various modifications and variations can be made in the processes and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

| | | DNA CODON | | | | AMINO ACID 3 LET. | | | | AMINO ACID 1 LET. | | | |
|---|---|---|---|---|---|---|---|---|---|---|---|---|---|
| | \2 | T | C | A | G | T | C | A | G | T | C | A | G |
| 1 | 3\ | | | | | | | | | | | | |
| | T | TTT | TCT | TAT | TGT | PHE | SER | TYR | CYS | F | S | Y | C |
| T | C | TTC | TCC | TAC | TGC | PHE | SER | TYR | CYS | F | S | Y | C |
| | A | TCA | TCA | TAA | TGA | LEU | SER | *** | *** | L | S | * | * |
| | G | TTG | TCG | TAG | TGG | LEU | SER | *** | TRP | L | S | * | W |
| | T | CTT | CCT | CAT | CGT | LEU | PRO | HIS | ARG | L | P | H | R |
| C | C | CTC | CCC | CAC | CGC | LEU | PRO | HIS | ARG | L | P | H | R |
| | A | CTA | CCA | CAA | CGA | LEU | PRO | GLN | ARG | L | P | O | R |
| | G | CTG | CCG | CAG | CGG | LEU | PRO | GLN | ARG | L | P | O | R |
| | T | ATT | ACT | AAT | AGT | ILE | THR | ASN | SER | I | T | N | S |
| A | C | ATC | ACC | AAC | AGC | ILE | THR | ASN | SER | I | T | N | S |
| | A | ATA | ACA | AAA | AGA | ILE | THR | LYS | ARG | I | T | K | R |
| | G | ATG | ACG | AAG | AGG | MET | THR | LYS | ARG | M | T | K | R |
| | T | GTT | GCT | GAT | GGT | VAL | ALA | ASP | GLY | V | A | D | G |
| G | C | GTC | GCC | GAC | GGC | VAL | ALA | ASP | GLY | V | A | D | G |
| | A | GTA | GCA | GAA | GGA | VAL | ALA | GLU | GLY | V | A | E | G |
| | G | GTG | GCG | GAG | GGG | VAL | ALA | GLU | GLY | V | A | E | G |

| 3 Letter | 1 Letter | CODONS |
|---|---|---|
| ALA | A | GCT GCC GCA GCG |
| ARG | R | CGT CGC CGA CGG AGA AGG |
| ASN | N | AAT AAC |
| ASP | D | GAT GAC |
| CYS | C | TGT TGC |
| GLN | O | CAA CAG |
| GLU | E | GAA GAG |
| GLY | G | GGT GGC CGA GGG |
| HIS | H | CAT CAC |
| ILE | I | ATT ATC ATA |
| LEU | L | CTT CTC CTA CTG TTA TTG |
| LYS | K | AAA AAG |
| MET | M | ATG |
| PHE | F | TTT TTC |
| PRO | P | CCT CCC CCA CCG |
| SER | S | TCT TCC TCA TCG AGT AGC |
| THR | T | ACT ACC ACA ACG |
| TRP | W | TGG |
| TYR | Y | TAT TAC |

| DNA CODON | | AMINO ACID 3 LET. | AMINO ACID 1 LET. |
|---|---|---|---|
| VAL | V | GTT GTC GTA GTG | |
| *** | * | TAA TAG TGA | |

What is claimed is:

1. A peptide comprising the gag precursor protein of human immunodeficiency virus type 2 (HIV-2$_{ROD}$—), wherein the peptide is free of particles of said virus, having the following amino acid sequence:

Met Gly Ala Arg Asn Ser Val Leu Arg Gly Lys Lys Ala Asp Glu Leu Glu Arg Ile Arg Leu

Arg Pro Gly Gly Lys Lys Lys Tyr Arg Leu Lys His Ile Val Trp Ala Ala Asn Lys Leu Asp

Arg Phe Gly Leu Ala Glu Ser Leu Leu Glu Ser Lys Glu Gly Cys Gln Lys Ile Leu Thr Val

Leu Asp Pro Met Val Pro Thr Gly Ser Glu Asn Leu Lys Ser Leu Phe Asn Thr Val Cys Val

Ile Trp Cys Ile His Ala Glu Glu Lys Val Lys Asp Thr Glu Gly Ala Lys Gln Ile Val Arg Arg

His Leu Val Ala Glu Thr Gly Thr Ala Glu Lys Met Pro Ser Thr Ser Arg Pro Thr Ala Pro Ser

Ser Glu Lys Gly Gly Asn Tyr Pro Val Gln His Val Gly Gly Asn Tyr Thr His Ile Pro Leu Ser

Pro Arg Thr Leu Asn Ala Trp Val Lys Leu Val Glu Glu Lys Lys Phe Gly Ala Glu Val Val

Pro Gly Phe Gln Ala Leu Ser Glu Gly Cys Thr Pro Tyr Asp Ile Asn Gln Met Leu Asn Cys

Val Gly Asp His Gln Ala Ala Met Gln Ile Ile Arg Glu Ile Ile Asn Glu Glu Ala Ala Glu Trp

Asp Val Gln His Pro Ile Pro Gly Pro Leu Pro Ala Gly Gln Leu Arg Glu Pro Arg Gly Ser

Asp Ile Ala Gly Thr Thr Ser Thr Val Glu Glu Gln Ile Gln Trp Met Phe Arg Pro Gln Asn Pro

Val Pro Val Gly Asn Ile Tyr Arg Arg Trp Ile Gln Ile Gly Leu Gln Lys Cys Val Arg Met Tyr

Asn Pro Thr Asn Ile Leu Asp Ile Lys Gln Gly Pro Lys Glu Pro Phe Gln Ser Tyr Val Asp

Arg Phe Tyr Lys Ser Leu Arg Ala Glu Gln Thr Asp Pro Ala Val Lys Asn Trp Met Thr Gln

Thr Leu Leu Val Gln Asn Ala Asn Pro Asp Cys Lys Leu Val Leu Lys Gly Leu Gly Met Asn

Pro Thr Leu Glu Glu Met Leu Thr Ala Cys Gln Gly Val Gly Gly Pro Gly Gln Lys Ala Arg

Leu Met Ala Glu Ala Leu Lys Glu Val Ile Gly Pro Ala Pro Ile Pro Phe Ala Ala Ala Gln Gln

Arg Lys Ala Phe Lys Cys Trp Asn Cys Gly Lys Glu Gly His Ser Ala Arg Gln Cys Arg Ala

Pro Arg Arg Gln Gly Cys Trp Lys Cys Gly Lys Pro Gly His Ile Met Thr Asn Cys Pro Asp

Arg Gln Ala Gly Phe Leu Gly Leu Gly Pro Trp Gly Lys Lys Pro Arg Asn Phe Pro Val Ala

Gln Val Pro Gln Gly Leu Thr Pro Thr Ala Pro Pro Val Asp Pro Ala Val Asp Leu Leu Glu

-continued

Lys Tyr Met Gln Gln Gly Lys Arg Gln Arg Glu Gln Arg Glu Arg Pro Tyr Lys Glu Val Thr

Glu Asp Leu Leu His Leu Glu Gln Gly Glu Thr Pro Tyr Arg Glu Pro Pro Thr Glu Asp Leu

Leu His Leu Asn Ser Leu Phe Gly Lys Asp Gln.

2. A peptide comprising the polymerase precursor protein of human immunodeficiency virus type 2 (HIV-$2_{ROD}$), wherein the peptide is free of particles of said virus, having the following amino acid sequence:

Thr Gly Arg Phe Phe Arg Thr Gly Pro Leu Gly Lys Glu Ala Pro Gln Leu Pro Arg Gly Pro
Ser Ser Ala Gly Ala Asp Thr Asn Ser Thr Pro Ser Gly Ser Ser Ser Gly Ser Thr Gly Glu Ile
Tyr Ala Ala Arg Glu Lys Thr Glu Arg Ala Glu Arg Glu Thr Ile Gln Gly Ser Asp Arg Gly
Leu Thr Aln Pro Arg Ala Gly Gly Asp Thr Ile Gln Gly Ala Thr Asn Arg Gly Leu Ala Ala
Pro Gln Phe Ser Leu Trp Lys Arg Pro Val Val Thr Ala Tyr Ile Glu Gly Gln Pro Val Glu Val
Leu Leu Asp Thr Thr Gly Ala Asp Asp Ser Ile Val Ala Ala Gly Ile Glu Leu Gly Asn Tyr Ser
Pro Lys Ile Val Gly Gly Ile Gly Gly Phe Ile Asn Thr Lys Glu Tyr Lys Asn Val Glu Ile Glu
Val Leu Asn Lys Lys Val Arg Ala Thr Ile Met Thr Gly Asp Thr Pro Ile Asn Ile Phe Gly Arg
Asn Ile Leu Thr Ala Leu Gly Met Ser Leu Gly Met Ser Leu Asn Leu Pro Val Ala Lys Val
Glu Pro Ile Lys Ile Met Leu Lys Pro Gly Lys Asp Gly Pro Lys Leu Arg Gln Trp Pro Leu Thr
Lys Glu Lys Ile Glu Ala Leu Lys Glu Ile Cys Glu Lys Met Glu Lys Glu Gly Gln Leu
Glu Glu Ala Pro Pro Thr Asn Pro Tyr Asn Thr Pro Thr Phe Ala Ile Lys Lys Lys Asp Lys
Asn Lys Trp Arg Met Leu Ile Asp Phe Arg Glu Leu Asn Lys Val Thr Gln Asp Phe Thr Glu
Ile Gln Leu Gly Ile Pro His Pro Ala Gly Leu Ala Lys Lys Arg Arg Ile Val Leu Asp Val
Gly Asp Ala Tyr Phe Ser Ile Pro Leu His Glu Asp Phe Arg Pro Tyr Thr Ala Phe Thr Leu
Pro Ser Val Asn Asn Ala Glu Pro Gly Lys Arg Tyr Ile Tyr Lys Val Leu Pro Gln Gly Trp
Lys Gly Ser Pro Ala Ile Phe Gln His Thr Met Arg Gln Val Leu Glu Pro Phe Arg Lys Ala
Asn Lys Asp Val Ile Ile Ile Gln Tyr Met Asp Asp Ile Leu Ile Ala Ser Asp Arg Thr Asp Leu
Glu His Asp Arg Val Val Leu Gln Leu Lys Glu Leu Leu Asn Gly Leu Gly Phe Ser Thr Pro
Asp Glu Lys Phe Gln Lys Asp Pro Pro Tyr His Trp Met Gly Tyr Glu Leu Trp Pro Thr Lys
Trp Lys Leu Gln Lys Ile Gln Leu Pro Gln Lys Glu Ile Trp Thr Val Asn Asp Ile Gln Lys Leu
Val Gly Val Leu Asn Trp Ala Ala Gln Leu Tyr Pro Gly Ile Lys Thr Lys His Leu Cys Arg
Leu Ile Arg Gly Lys Met Thr Leu Thr Glu Glu Val Gln Trp Thr Glu Leu Ala Glu Ala Glu
Leu Glu Glu Asn Arg Ile Ile Leu Ser Gln Glu Gln Glu Gly His Tyr Tyr Gln Glu Glu Lys Glu
Leu Glu Ala Thr Val Gln Lys Asp Gln Glu Asn Gln Trp Thr Tyr Lys Ile His Gln Glu Glu Lys
Ile Leu Lys Val Gly Lys Tyr Ala Lys Val Lys Asn Thr His Thr Asn Gly Ile Arg Leu Leu
Ala Gln Val Val Gln Lys Ile Gly Lys Glu Ala Leu Val Ile Trp Gly Arg Ile Pro Lys Phe His
Leu Pro Val Glu Arg Glu Ile Trp Glu Gln Trp Trp Asp Asn Tyr Trp Gln Val Thr Trp Ile Pro
Asp Trp Asp Phe Val Ser Thr Pro Pro Leu Val Arg Leu Ala Phe Asn Leu Val Gly Asp Pro
Ile Pro Gly Ala Glu Thr Phe Tyr Thr Asp Gly Ser Cys Asn Arg Gln Ser Lys Glu Gly Lys
Ala Gly Tyr Val Thr Asp Arg Gly Lys Asp Lys Val Lys Lys Leu Glu Gln Thr Thr Asn Gln
Gln Ala Glu Leu Glu Ala Phe Ala Met Ala Leu Thr Asp Ser Gly Pro Lys Val Asn Ile Ile Val
Asp Ser Gln Tyr Val Met Gly Ile Ser Ala Ser Gln Pro Thr Glu Ser Glu Ser Lys Ile Val Asn
Gln Ile Ile Glu Glu Met Ile Lys Lys Glu Ala Ile Tyr Val Trp Val Pro Ala His Lys Gly
Ile Gly Gly Asn Gly Glu Val Asp His Leu Val Ser Gln Gly Ile Arg Gln Val Leu Phe Leu
Glu Lys Ile Glu Pro Ala Gln Glu Glu His Glu Lys Tyr His Ser Asn Val Lys Glu Ser His

-continued

Lys Phe Gly Ile Pro Asn Leu Val Ala Arg Gln Ile Val Asn Ser Cys Ala Gln Cys Ala Gln Cys

Gln Gln Lys Gly Glu Ala Ile His Gly Gln Val Asn Ala Glu Leu Gly Thr Trp Gln Met Asp

Cys Thr Leu Glu Gly Lys Ile Ile Ile Val Ala Val His Val Ala Ser Gly Phe Ile Glu Ala

Glu Val Ile Pro Gln Glu Ser Gly Arg Gln thr Ala Leu Phe Leu Leu Lys Leu Ala Ser Arg Trp Pro Ile Thr His Leu His Thr Asp Asn Gly Ala Asn Phe Thr Ser Gln Glu Val Lys Met Val Ala Trp Trp Ile Gly Ile Glu Gln Ser Phe Gly Val Pro Tyr Asn Pro Gln Ser Gln Gly Val Val Glu Ala Met Asn His His Leu Lys Asn Gln Ile Ser Arg Ile Arg Glu Gln Ala asn Thr Ile Glu Thr Ile Val Leu Met Ala Ile His Cys Met Asn Phe Lys Arg Arg Gly Gly Ile Gly Asp Met Thr Pro Ser Glu Arg Leu Ile Asn Met Ile Thr Thr Glu Gln Glu Ile Gln Phe Leu Gln Ala Lys Asn Ser Lys Leu Lys Asp Phe Arg Val Tyr Phe Arg Glu Gly Arg Asp Gln Leu Trp Lys Gly Pro Gly Glu Leu Leu Trp Lys Gly Glu Gly Ala Val Leu Val Lys Val Gly Thr Asp Ile Lys Ile Ile Pro Arg Arg Lys Ala Lys Ile Ile Arg Asp Tyr Gly Gly Arg Gln Glu Met Asp Ser Gly Ser His Leu Glu Gly Ala Arg Glu Asp Gly Glu Met Ala.

3. A peptide comprising the Vif protein of human immunodeficiency virus type 2 (HIV-2$_{ROD}$), wherein the peptide is free of particles of said virus, having the following amino acid sequence:

Met Glu Glu Asp Lys Arg Trp Ile Val Val Pro Thr Trp Arg Val Pro Gly Arg Met Glu Lys
Trp His Ser Leu Val Lys Tyr Leu Lys Tyr Lys Thr Lys Asp Leu Glu Lys Val Cys Tyr Val
Pro His His Lys Val Gly Trp Ala Trp Trp Thr Cys Ser Arg Val Ile Phe Pro Leu Lys Gly Asn
Ser his Leu Glu Ile Gln Ala Tyr Trp Asn Leu Thr Pro Glu Lys Gly Trp Leu Ser Ser Tyr Ser
Val Arg Ile Thr Trp Tyr Thr Glu Lys Phe Trp Thr Asp Val Thr Pro Asp Cys Ala Asp Val
Leu Ile His Ser Thr Tyr Phe Pro Cys Phe Thr Ala Gly Glu Val Arg Arg Ala Ile Arg Gly Glu
Lys Leu Leu Ser Cys Cys Asn Tyr Pro Arg Ala His Arg Ala Gln Val Pro Ser Leu Gln Phe
Leu Ala Leu Val Val Val Gln Gln Asn Asp Arg Pro Gln Arg Asp Ser Thr Thr Arg Lys Gln
Arg Arg Arg Asp Tyr Arg Arg Gly Leu Arg Leu Ala Lys Gln Asp Ser Arg Ser His Lys Gln
Arg Ser Ser Glu Ser Pro Thr Pro Arg Thr Tyr Phe Pro Gly Val Ala Glu Val Leu Glu Ile Leu
Ala.

4. A peptide comprising the Vpr protein of human immunodeficiency virus type 2 (HIV-$2_{ROD}$), wherein the peptide is free of particles of said virus, having the following amino acid sequence:

Met Ala Glu Ala Pro Thr Glu Leu Pro Pro Val Asp Gly Thr Pro Leu Arg Glu Pro Gly Asp
Glu Trp Ile Ile Glu Ile Leu Arg Glu Ile Lys Glu Glu Ala Leu Lys His Phe Asp Pro Arg Leu
Leu Ile Ala Leu Gly Lys Try Ile Tyr Thr Arg His Gly Asp Thr Leu Glu Gly Ala Arg Glu

Leu Ile Lys Val Leu Gln Arg Ala Leu Phe Thr His Phe Arg Ala Gly Cys Gly His Ser Arg Ile Gly Gln Thr Arg Gly Gly Asn Pro Leu Ser Ala Ile Pro Thr Pro Arg Asn Met Gln.

5. A peptide comprising the Vpx protein of human immunodeficiency virus type 2 (HIV-2$_{ROD}$), wherein the peptide is free of particles of said virus, having the following amino acid sequence:

Met Thr Asp Pro Arg Glu Thr Val Pro Pro Gly Asn Ser Gly Glu Glu Thr Ile Gly Glu Ala

Phe Ala Trp Leu Asn Arg Thr Val Glu Ala Ile Asn Arg Glu Ala Val Asn His Leu Pro Arg

Glu Leu Ile Phe Gln Val Trp gln Arg Ser Trp Arg Tyr Trp His Asp Glu Gln Gly Met Ser Glu Ser Tyr Thr Lys Tyr Arg Tyr Leu Cys Ile Ile Gln Lys Ala Val Tyr Met His Val Arg Lys Gly Cys Thr Cys Leu Gly Arg Gly His Gly Pro Gly Gly Trp Arg Pro Gly Pro Pro Pro Pro Pro Pro Gly Leu Val.

6. A peptide comprising the Nef protein of human immunodeficiency virus type 2 (HIV-2$_{ROD}$), wherein the peptide is free of particles of said virus, having the following amino acid sequence:

Met Gly Ala Ser Gly Ser Lys Lys His Ser Arg Pro Pro Arg Gly Leu Gln Glu Arg Leu Leu

Arg Ala Arg Ala Gly Ala Cys Gly Gly Tyr Trp Asn Glu Ser Gly Gly Glu Tyr Ser Arg Phe

Gln Glu Gly Ser Asp Arg Glu Gln Lys Ser Pro Ser Cys Glu Gly Arg Gln Tyr Gln Gln Gly

Asp Phe Met Asn Thr Pro Trp Lys Asp Pro Ala Ala Glu Arg Glu Lys Asn Leu Try Arg Gln

Gln Asn Met Asp Asp Val Asp Ser Asp Asp Asp Gln Val Arg Val Ser Val Thr Pro Lys

Val Pro Leu Arg Pro Met Thr His Arg Leu Ala Ile Asp Met Ser His Leu Ile Lys Thr Arg Gly

Gly Leu Glu Gly Met Phe Tyr Ser Glu Arg Arg His Lys Ile Leu Asn Ile Tyr Leu Glu Lys

Glu Glu Gly Ile Ile Ala Asp Trp Gln Asn Tyr Thr His Gly Pro Gly Val Arg Tyr Pro Met Phe

Phe Gly Trp Leu Trp Lys Leu Val Pro Val Asp Val Pro Gln Glu Gly Glu Asp Thr Glu Thr

His Cys Leu Val His Pro Ala Gln Thr Ser Lys Phe Asp Asp Pro His Gly Glu Thr Leu Val

Trp Glu Phe Asp Pro Leu Leu Ala Tyr Ser Tyr Glu Ala Phe Ile Arg Tyr Pro Glu Glu Phe

Gly His Lys Ser Gly Leu Pro Glu Glu Glu Trp Lys Ala Arg Leu Lys Ala Arg Gly Ile Pro

Phe Ser.

7. A peptide comprising the TAT protein of human immunodeficiency virus type 2 (HIV-2$_{ROD}$), wherein the peptide is free of particles of said virus, having the following amino acid sequence:

Met Glu Thr Pro Leu Lys Ala Pro Glu Ser Ser Leu Lys Ser Cys Asn Glu Pro Phe Ser Arg

Thr Ser Glu Gln Asp Val Ala Thr Gln Glu Leu Ala Arg Gln Gly Glu Glu Ile Leu Ser Gln

Leu Tyr Arg Pro Leu Glu Thr Cys Asn Asn Ser Cys Tyr Cys Lys Arg Cys Cys Tyr His Cys

Gln Met Cys Phe Leu Asn Lys Gly Leu Gly Ile Cys Tyr Glu Arg Lys Gly Arg Arg Arg

Thr Pro Lys Lys Thr Lys Thr His Pro Ser Pro Thr Pro Asp Lys; and

Ser Ile Ser Thr Arg Thr Gly Asp Ser Gln Pro Thr Lys Lys Gln Lys Lys Thr Val Glu Ala Thr

Val Glu Thr Asp Thr Gly Pro Gly Arg.

8. A peptide comprising the Rev protein of human immunodeficiency virus type 2 (HIV-2$_{ROD}$), wherein the peptide is free of particles of said virus, having the following amino acid sequence:

Met Asn Glu Arg Ala Asp Glu Glu Gly Leu Gln Arg Lys Leu Arg Leu Ile Arg Leu Leu His

Gln Thr; and

Asn Pro Tyr Pro Gln Gly Pro Gly Thr Ala Ser Gln Arg Arg Asn Arg Arg Arg Arg Trp Lys

Gln Arg Trp Arg Gln Ile Leu Ala Leu Ala Asp Ser Ile Tyr Thr Phe Pro Asp Pro Pro Ala Asp

Ser Pro Leu Asp Gln Thr Ile Gln His Leu Gln Gly Leu Thr Ile Gln Glu Leu Pro Asp Pro Pro

Thr His Leu Pro Glu Ser Gln Arg Leu Ala Glu Thr.

9. An in vitro diagnostic method for the detection of the presence or absence of antibodies which bind to antigens of a human immunodeficiency virus type 2 (HIV-2) comprising:
  (a) contacting a biological sample with one or more peptides selected from the group consisting of:
    (1) a peptide comprising the gag precursor protein of human immunodeficiency virus type 2 (HIV-2$_{ROD}$), having the following sequence:

Met Gly Ala Arg Asn Ser Val Leu Arg Gly Lys Lys Ala Asp Glu

Leu Glu Arg Ile Arg Leu Arg Pro Gly Gly Lys Lys Lys Tyr Arg

Leu Lys His Ile Val Trp Ala Ala Asn Lys Leu Asp Arg Phe Gly

Leu Ala Glu Ser Leu Leu Glu Ser Leu Glu Gly Cys Gln Lye Ile

Leu Thr Val Leu Asp Pro Met Val Pro Thr Gly Ser Glu Asn Leu

Lys Ser Leu Phe Asn Thr Val Cys Val Ile Trp Cys Ile His Ala

Glu Glu Lys Val Lys Asp Thr Glu Gly Ala Lys Gln Ile Val Arg

Arg His Leu Val Ala Glu Thr Gly Thr Ala Glu Lys Met Pro Ser

Thr Ser Arg Pro Thr Ala Pro Ser Ser Glu Lys Gly Gly Asn Tyr

Pro Val Gln His Val Gly Gly Asn Tyr Thr His Ile Pro Leu Ser

Pro Arg Thr Leu Asn Ala Trp Val Lys Leu Val Glu Glu Lys Lys

-continued

Phy Gly Ala Glu Val Val Pro Gly Phe Gln Ala Leu Ser Glu Gly

Cys Thr Pro Tyr Asp Ile Asn Gln Met Leu Asn Cys Val Gly Asp

His Gln Ala Ala Met Gln Ile Ile Arg Glu Ile Ile Asn Glu Glu Ala

Ala Glu Trp Asp Val Gln His Pro Ile Pro Gly Pro Leu Pro Ala

Gly Gln Leu Arg Glu Pro Arg Gly Ser Asp Ile Ala Gly Thr Thr

Ser Thr Val Glu Glu Gln Ile Gln Trp Met Phe Arg Pro Gln Asn

Pro Val Pro Val Gly Asn Ile Tyr Arg Arg Trp Ile Gln Ile Gly

Leu Gln Lys Cys Val Arg Met Thr Asn Pro Thr Asn Ile Leu Asp

Ile Lys Gln Gly Pro Lys Glu Pro Phe Gln Ser Tyr Val Asp Arg

Phe Tyr Lys Ser Leu Arg Ala Glu Gln Thr Asp Pro Ala Val Lys

Asn Trp Met Thr Gln Thr Leu Leu Val Gln Asn Ala Asn Pro Asp

Cys Lys Leu Val Leu Lys Gly Leu Gly Met Asn Pro Thr Leu Glu

Glu Met Leu Thr Ala Cys Gln Gly Val Gly Gly Pro Gly Gln Lys

Ala Arg Leu Met Ala Glu Ala Leu Lys Glu Val Ile Gly Pro Ala

Pro Ile Pro Phe Ala Ala Ala Gln Gln Arg Lys Ala Phe Lys Cys

Trp Asn Cys Gly Lys Glu Gly His Ser Ala Arg Gln Cys Arg Ala

Pro Arg Arg Gln Gly Cys Trp Lys Cys Gly Lys Pro Gly His Ile

Met Thr Asn Cys Pro Asp Arg Gln Ala Gly Phe Leu Gly Leu Gly

Pro Try Gly Lys Lys Pro Arg Asn Phe Pro Val Ala Gln Val Pro

Gln Gly Leu Thr Pro Thr Ala Pro Pro Val Asp Pro Ala Val Asp

Leu Leu Gln Lys Tyr Met Gln Gln Gly Lys Arg Gln Arg Glu Gln

Arg Glu Arg Pro Tyr Lys Glu Val Thr Glu Asp Leu Leu His Leu

Glu Gln Gly Glu Thr Pro Tyr Arg Glu Pro Pro Thr Glu Asp Leu Leu His Leu Asn Ser Leu Phe Gly Lys Asp Gln;

(2) a peptide comprising the polymerase precursor protein of human immunodeficiency virus type 2 (HIV-$2_{ROD}$), having the following sequence:

Thr Gly Arg Phe Phe Arg Thr Gly Pro Leu Gly Lys Glu Ala Pro Gln Leu Pro Arg Gly Pro Ser Ser Ala Gly Ala Asp Thr Asn Ser Thr Pro Ser Gly Ser Ser Ser Gly Ser Thr Gly Glu Ile Tyr Ala Ala Arg Glu Lys Thr Glu Arg Ala Glu Arg Glu Thr Ile Gln Gly Ser Asp Arg Gly Leu Thr Aln Pro Arg Ala Gly Gly Asp Thr Ile Gln Gly Ala Thr Asn Arg Gly Leu Ala Ala Pro Gln Phe Ser Leu Trp Lys Arg Pro Val Val Thr Ala Tyr Ile Glu Gly Gln Pro Val Glu Val Leu Leu Asp Thr Gly Ala Asp Asp Ser Ile Val Ala Gly Ile Glu Leu Gly Asn Asn Tyr Ser Pro Lys Ile Val Gly Gly Ile Gly Gly Phe Ile Asn Thr Lys Glu Tyr Lys Asn Val Glu Ile Glu Val Leu Asn Lys Lys Val Arg Ala Thr Ile Met Thr Gly Asp Thr Pro Ile Asn Ile Phe Gly Arg Asn Ile Leu Thr Ala Leu Gly Met Ser Leu Gly Met Ser Leu Asn Leu Pro Val Ala Lys Val Glu Pro Ile Lys Ile Met Leu Lys Pro Gly Lys Asp Gly Pro Lys Leu Arg Gln Trp Pro Leu Thr Lys Glu Lys Ile Glu Ala Leu Lys Glu Ile Cys Glu Lys Met Glu Lys Glu Gly Gln Leu Glu Glu Ala Pro Pro Thr Asn Pro Tyr Asn Thr Pro Thr Phe Ala Ile Lys Lys Lys Asp Lys Asn Lys Trp Arg Met Leu Ile Asp Phe Arg Glu Leu Asn Lys Val Thr Gln Asp Phe Thr Glu Ile Gln Leu Gly Ile Pro His Pro Ala Gly Leu Ala Lys Lys Arg Arg Ile Thr Val Leu Asp Val Gly Asp Ala Tyr Phe Ser Ile Pro Leu His Glu Asp Phe Arg Pro Tyr Thr Ala Phe Thr Leu Pro Ser Val Asn Asn Ala Glu Pro Gly Lys Arg Tyr Ile Tyr Lys Val Leu Pro Gln Gly Trp Lys Gly Ser Pro Ala Ile Phe Gln His Thr Met Arg Gln Val Leu Glu Pro Phe Arg Lys Ala Asn Lys Asp Val Ile Ile Ile Gln Tyr Met Asp Asp Ile Leu Ile Ala Ser Asp Arg Thr Asp Leu Glu His Asp Arg Val Val Leu Gln Leu Lys Glu Leu Leu Asn Gly Leu Gly Phe Ser Thr Pro Asp Glu Lys Phe Gln Lys Asp Pro Pro Tyr His Trp Met Gly Tyr Glu Leu Trp Pro Thr Lys Trp Lys Leu Gln Lys Ile Gln Leu Pro Gln Lys Glu Ile Trp Thr Val Asn Asp Ile Gln Lys Leu Val Gly Val Leu Asn Trp Ala Ala Gln Leu Tyr Pro Gly Ile Lys Thr Lys His Leu Cys Arg Leu Ile Arg Gly Lys Met Thr Leu Thr Glu Glu Val Gln Trp Thr Glu Leu Ala Glu Ala Glu Leu Glu Glu Asn Arg Ile

-continued

Ile Leu Ser Gln Glu Gln Glu Gly His Tyr Tyr Gln Glu Glu Lys Glu Leu Glu Ala Thr Val Gln Lys Asp Gln Glu Asn Gln Trp Thr Tyr Lys Ile His Gln Glu Glu Lys Ile Leu Lys Val Gly Lys Tyr Ala Lys Val Lys Asn Thr His Thr Asn Gly Ile Arg Leu Leu Ala Gln Val Val Gln Lys Ile Gly Lys Glu Ala Leu Val Ile Trp Gly Arg Ile Pro Lys Phe His Leu Pro Val Gln Arg Glu Ile Trp Glu Gln Trp Trp Asp Asn Tyr Trp Gln Val Thr Trp Ile Pro Asp Trp Asp Phe Val Ser Thr Pro Pro Leu Val Arg Leu Ala Phe Asn Leu Val Gly Asp Pro Ile Pro Gly Ala Glu Thr Phe Tyr Thr Asp Gly Ser Cys Asn Arg Gln Ser Lys Glu Gly Lys Ala Gly Tyr Val Thr Asp Arg Gly Lys Asp Lys Val Lys Lys Leu Glu Gln Thr Thr Asn Gln Gln Ala Glu Leu Glu Ala Phe Ala Met Ala Leu Thr Asp Ser Gly Pro Lys Val Asn Ile Ile Val Asp Ser Gln Tyr Val Met Gly Ile Ser Ala Ser Gln Pro Thr Glu Ser Glu Ser Lys Ile Val Asn Gln Ile Ile Glu Glu Met Ile Lys Lys Glu Ala Ile Tyr Val Ala Trp Val Pro Ala His Lys Gly Ile Gly Gly Asn Gly Glu Val Asp His Leu Val Ser Gln Gly Ile Arg Gln Val Leu Phe Leu Glu Lys Ile Glu Pro Ala Gln Glu Glu His Glu Lys Tyr His Ser Asn Val Lys Glu Leu Ser His Lys Phe Gly Ile Pro Asn Leu Val Ala Arg Gln Ile Val Asn Ser Cys Ala Gln Cys Ala Gln Cys Gln Gln Lys Gly Glu Ala Ile His Gly Gln Val Asn Ala Glu Leu Gly Thr Trp Gln Met Asp Cys Thr His Leu Glu Gly Lys Ile Ile Ile Val Ala Val His Val Ala Ser Gly Phe Ile Glu Ala Glu Val Ile Pro Gln Glu Ser Gly Arg Gln thr Ala Leu Phe Leu Leu Lys Leu Ala Ser Arg Trp Pro Ile Thr His Leu His Thr Asp Asn Gly Ala Asn Phe Thr Ser Gln Glu Val Lys Met Val Ala Trp Trp Ile Gly Ile Glu Gln Ser Phe Gly Val Pro Tyr Asn Pro Gln Ser Gln Gly Val Val Glu Ala Met Asn His His Leu Lys Asn Gln Ile Ser Arg Ile Arg Glu Glu Ala asn Thr Ile Glu Thr Ile Val Leu Met Ala Ile His Cys Met Asn Phe Lys Arg Arg Gly Gly Ile Gly Asp Met Thr Pro Ser Glu Arg Leu Ile Asn Met Ile Thr Thr Glu Gln Glu Ile Gln Phe Leu Gln Ala Lys Asn Ser Lys Leu Lys Asp Phe Arg Val Tyr Phe Arg Glu Gly Arg Asp Gln Leu Trp Lys Gly Pro Gly Glu Leu Leu Trp Lys Gly Glu Gly Ala Val Leu Val Lys Val Gly Thr Asp Ile Lys Ile Ile Pro Arg Arg Lys Ala Lys Ile Ile Arg Asp Tyr Gly Gly Arg Gln Glu Met Asp Ser Gly Ser His Leu Glu Gly Ala Arg Glu Asp Gly Glu Met Ala;

(3) a peptide comprising the env precursor protein of human immunodeficiency virus type 2 (HIV-$2_{ROD}$), having the following sequence:

Met Met Asn Gln Leu Leu Ile Ala Ile Leu Leu Ala Ser Ala Cys Leu Val Tyr Cys Thr Gln Tyr Val Thr Val Phe Tyr Gly Val Pro Thr Trp Lys Asn Ala Thr Thr Pro Leu Phe Cys Ala Thr Arg Asn Arg Asp Thr Trp Gly Thr Ile Gln Cys Leu Pro Asp Asn Asp Asp Tyr Gln Glu Ile

-continued

Thr Leu Asn Val Thr Glu Ala Phe Asp Ala Trp Asn Asn Thr Val Thr

Glu Gln Ala Ile Glu Asp Val Trp His Leu Phe Glu Thr Ser Ile Lys

Pro Cys Val Lys Leu Thr Pro Leu Cys Val Ala Met Lys Cys Ser Ser

Thr Glu Ser Ser Thr Gly Asn Asn Thr Thr Ser Lys Ser Thr Ser Thr

Thr Thr Thr Thr Pro Thr Asp Gln Glu Gln Glu Ile Ser Glu Asp Thr

Pro Cys Ala Arg Ala Asp Asn Cys Ser Gly Leu Gly Glu Glu Glu Thr

Ile Asn Cys Gln Phe Asn Met Thr Gly Leu Glu Arg Asp Lys Lys Lys

Gln Tyr Asn Glu Thr Trp Tyr Ser Lys Asp Val Val Cys Glu Thr Asn

Asn Ser Thr Asn Gln Thr Gln Cys Tyr Met Asn His Cys Asn Thr Ser

Val Ile Thr Glu Ser Cys Asp Lys His Tyr Trp Asp Ala Ile Arg Phe

Arg Tyr Cys Ala Pro Pro Gly Tyr Ala Leu Leu Arg Cys Asn Asp Thr

Asn Tyr Ser Gly Phe Ala Pro Asn Cys Ser Lys Val Val Ala Ser Thr

Cys Thr Arg Met Met Glu Thr Gln Thr Ser Thr Trp Phe Gly Phe Asn

Gly Thr Arg Ala Glu Asn Arg Thr Tyr Ile Tyr Trp His Gly Arg Asp

Asn Arg Thr Ile Ile Ser Leu Asn Lys Tyr Tyr Asn Leu Ser Leu His

Cys Lys Arg Pro Gly Asn Lys Thr Val Lys Gln Ile Met Leu Met Ser

Gly His Val Phe His Ser His Tyr Gln Pro Ile Asn Lys Arg Pro Arg

Gln Ala Trp Cys Trp Phe Lys Gly Lys Trp Lys Asp Ala Met Gln Glu

Val Lys Glu Thr Leu Ala Lys His Pro Arg Tyr Arg Gly Thr Asn Asp

Thr Arg Asn Ile Ser Phe Ala Ala Pro Gly Lys Gly Ser Asp Pro Glu

Val Ala Tyr Met Trp Thr Asn Cys Arg Gly Glu Phe Leu Tyr Cys Asn

Met Thr Trp Phe Leu Asn Trp Ile Glu Asn Lys Thr His Arg Asn Tyr

Ala Pro Cys His Ile Lys Gln Ile Ile Asn Thr Trp His Lys Val Gly

Arg Asn Val Tyr Leu Pro Pro Arg Glu Gly Glu Leu Ser Cys Asn Ser

Thr Val Thr Ser Ile Ile Ala Asn Ile Asp Trp Gln Asn Asn Asn Gln thr Asn Ile Thr Phe Ser Ala Glu Val Ala Glu Leu Tyr Arg Leu Glu Leu Gly Asp Tyr Lys leu Val Glu Ile Thr Pro Ile Gly Phe Ala Pro Thr Lys Glu Lys Arg Tyr Ser Ser Ala His Gly Arg His Thr Arg Gly Val Phe Val Leu Gly Phe Leu Gly Phe Leu Ala Thr Ala Gly Ser Ala Met Gly Ala Ala Ser Leu Thr Val Ser Ala Gln Ser Arg Thr Leu Leu Ala Gly Ile Val Gln Gln Gln Gln Leu Leu Asp Val Val Lys Arg Gln Gln Glu Leu Leu Arg Leu Thr Val Trp Gly Thr Lys Asn Leu Gln Ala Arg Val Thr Ala Ile Glu Lys Tyr Leu Gln Asp Gln Ala Arg Leu Asn Ser Trp Gly Cys Ala Phe Arg Gln Val Cys His Thr Thr Val Pro Trp Val Asn Asp Ser Leu Ala Pro Asp Trp Asp Asn Met Thr Trp Gln Glu Trp Glu Lys Gln Val Arg Tyr Leu Glu Ala Asn Ile Ser Lys Ser Leu Glu Gln Ala Gln Ile Gln Gln Glu Lys Asn Met Tyr Glu Leu Gln Lys Leu Asn Ser Trp Asp Ile Phe Gly Asn Trp Phe Asp Leu Thr Ser Trp Val Lys Tyr Ile Gln Tyr Gly Val Leu Ile Ile Val Ala Val Ile Ala Leu Arg Ile Val Ile Tyr Val Val Gln Met Leu Ser Arg Leu Arg Lys Gly Tyr Arg Pro Val Phe Ser Ser Pro Pro Gly Tyr Ile Gln Gln Ile His Ile His Lys Asp Arg Gly Gln Pro Ala Asn Glu Glu Thr Glu Glu Asp Gly Gly Ser Asn Gly Gly Asp Arg Tyr Trp Pro Trp Pro Ile Ala Tyr Ile His Phe Leu Ile Arg Gln Leu Ile Arg Leu Leu Thr Arg Leu Tyr Ser Ile Cys Arg Asp Leu Leu Ser Arg Ser Phe leu Thr Leu Gln leu Ile Tyr Gln Asn Leu Arg Asp Trp Leu Arg Leu Arg Thr Ala Phe Leu Gln Tyr Gly Cys Glu Trp Ile Gln Glu Ala Phe Gln Ala Ala Ala Arg Ala Thr Arg Glu Thr Leu Ala Gly Ala Cys Arg Gly Leu Trp Arg Val Leu Glu Arg Ile Gly Arg Gly Ile Leu Ala Val Pro Arg Arg Ile Arg Gln Gly Ala Glu Ile Ala Leu Leu;

(4) a peptide comprising the Vif protein of human immunodeficiency virus type 2 (HIV-2$_{ROD}$), having the following sequence:

Met Glu Glu Asp Lys Arg Trp Ile Val Val

Pro Thr Trp Arg Val Pro Gly Arg Met Glu Lys

Trp His Ser Leu Val Lys Tyr Leu Lys Tyr

Lys Thr Lys Asp Leu Glu Lys Val Cys Tyr Val

Pro His His Lys Val Gly Trp Ala Trp Trp

Thr Cys Ser Arg Val Ile Phe Pro Leu Lys Gly

Asn Ser his Leu Glu Ile Gln Ala Tyr Trp Asn

Leu Thr Pro Glu Lys Gly Trp Leu Ser Ser

Tyr Ser Val Arg Ile Thr Trp Tyr Thr Glu Lys

Phe Trp Thr Asp Val Thr Pro Asp Cys Ala

Asp Val Leu Ile His Ser Thr Tyr Phe Pro Cys

Phe Thr Ala Gly Glu Val Arg Arg Ala Ile

Arg Gly Glu Lys Leu Leu Ser Cys Cys Asn Tyr

Pro Arg Ala His Arg Ala Gln Val Pro Ser

Leu Gln Phe Leu Ala Leu Val Val Val Gln Gln

Asn Asp Arg Pro Gln Arg Asp Ser Thr Thr

Arg Lys Gln Arg Arg Arg Asp Tyr Arg Arg Gly

Leu Arg Leu Ala Lys Gln Asp Ser Arg Ser

His Lys Gln Arg Ser Ser Glu Ser Pro Thr Pro Arg

Thr Tyr Phe Pro Gly Val Ala Glu Val

Leu Glu Ile Leu Ala;

(5) a peptide comprising the Vpr protein of human immunodeficiency virus type 2 (HIV-2$_{ROD}$), having the following sequence:

Met Ala Glu Ala Pro Thr Glu Leu Pro Pro Val

Asp Gly Thr Pro Leu Arg Glu Pro Gly Asp

Glu Trp Ile Ile Glu Ile Leu Arg Glu Ile Lys Glu

Glu Ala Leu Lys His Phe Asp Pro Arg Leu

Leu Ile Ala Leu Gly Lys Try Ile Tyr Thr Arg

His Gly Asp Thr Leu Glu Gly Ala Arg Glu

Leu Ile Lys Val Leu Gln Arg Ala Leu Phe Thr

His Phe Arg Ala Gly Cys Gly His Ser Arg

Ile Gly Gln Thr Arg Gly Gly Asn Pro Leu Ser

Ala Ile Pro Thr Pro Arg Asn Met Gln;

(6) a peptide comprising the Vpx protein of human immunodeficiency virus type 2 (HIV-2$_{ROD}$), having the following sequence:

Met Thr Asp Pro Arg Glu Thr Val Pro Pro Gly

Asn Ser Gly Glu Glu Thr Ile Gly Glu Ala

Phe Ala Trp Leu Asn Arg Thr Val Glu Ala Ile

Asn Arg Glu Ala Val Asn His Leu Pro Arg

Glu Leu Ile Phe Gln Val Trp gln Arg Ser Trp

Arg Tyr Trp His Asp Glu Gln Gly Met Ser

Glu Ser Tyr Thr Lys Tyr Arg Tyr Leu Cys Ile

Ile Gln Lys Ala Val Tyr Met His Val Arg

Lys Gly Cys Thr Cys Leu Gly Arg Gly His Gly

Pro Gly Gly Trp Arg Pro Gly Pro Pro Pro

Pro Pro Pro Pro Gly Leu Val;

(7) a peptide comprising the Nef protein of human immunodeficiency virus type 2 (HIV-2$_{ROD}$), having the following sequence:

Met Gly Ala Ser Gly Ser Lys Lys His Ser Arg

Pro Pro Arg Gly Leu Gln Glu Arg Leu Leu

Arg Ala Arg Ala Gly Ala Cys Gly Gly Tyr Trp

Asn Glu Ser Gly Gly Glu Tyr Ser Arg Phe

Gln Glu Gly Ser Asp Arg Glu Gln Lys Ser Pro

Ser Cys Glu Gly Arg Gln Tyr Gln Gln Gly

Asp Phe Met Asn Thr Pro Trp Lys Asp Pro Ala

Ala Glu Arg Glu Lys Asn Leu Try Arg Gln

Gln Asn Met Asp Asp Val Asp Ser Asp Asp Asp

Asp Gln Val Arg Val Ser Val Thr Pro Lys

Val Pro Leu Arg Pro Met Thr His Arg Leu Ala

Ile Asp Met Ser His Leu Ile Lys Thr Arg

Gly Gly Leu Glu Gly Met Phe Tyr Ser Glu Arg

Arg His Lys Ile Leu Asn Ile Tyr Leu Glu

Lys Glu Glu Gly Ile Ile Ala Asp Trp Gln Asn

Tyr Thr His Gly Pro Gly Val Arg Tyr Pro

Met Phe Phe Gly Trp Leu Trp Lys Leu Val Pro

Val Asp Val Pro Gln Glu Gly Glu Asp Thr

Glu Thr His Cys Leu Val His Pro Ala Gln Thr

Ser Lys Phe Asp Asp Pro His Gly Glu Thr

Leu Val Trp Glu Phe Asp Pro Leu Leu Ala Tyr

Ser Tyr Glu Ala Phe Ile Arg Tyr Pro Glu

Glu Phe Gly His Lys Ser Gly Leu Pro Glu Glu

Glu Trp Lys Ala Arg Leu Lys Ala Arg Gly

Ile Pro Phe Ser;

(8) a peptide comprising the TAT protein of human immunodeficiency virus type 2 (HIV-2$_{ROD}$), having the following sequence:

Met Glu Thr Pro Leu Lys Ala Pro Glu Ser Ser

Leu Lys Ser Cys Asn Glu Pro Phe Ser Arg

Thr Ser Glu Gln Asp Val Ala Thr Gln Glu Leu

Ala Arg Gln Gly Glu Glu Ile Leu Ser Gln

Leu Tyr Arg Pro Leu Glu Thr Cys Asn Asn Ser

Cys Tyr Cys Lys Arg Cys Cys Tyr His Cys

Gln Met Cys Phe Leu Asn Lys Gly Leu Gly Ile

Cys Tyr Glu Arg Lys Gly Arg Arg Arg Arg

Thr Pro Lys Lys Thr Lys Thr His Pro Ser Pro

Thr Pro Asp Lys; and

Ser Ile Ser Thr Arg Thr Gly Asp Ser Gln Pro

Thr Lys Lys Gln Lys Lys Thr Val Glu Ala

Thr Val Glu Thr Asp Thr Gly Pro Gly Arg;

(9) a peptide comprising the Rev protein of human immunodeficiency virus type 2 (HIV-2$_{ROD}$), having the following sequence:

Met Asn Glu Arg Ala Asp Glu Glu Gly Leu Gln

Arg Lys Leu Arg Leu Ile Arg Leu Leu His

Gln Thr; and

Asn Pro Tyr Pro Gln Gly Pro Gly Thr Ala Ser

Gln Arg Arg Asn Arg Arg Arg Arg Trp Lys

Gln Arg Trp Arg Gln Ile Leu Ala Leu Ala Asp

Ser Ile Tyr Thr Phe Pro Asp Pro Pro Ala

Asp Ser Pro Leu Asp Gln Thr Ile Gln His Leu

Gln Gly Leu Thr Ile Gln Glu Leu Pro Asp

Pro Pro Thr His Leu Pro Glu Ser Gln Arg Leu

Ala Glu Thr;

(10) a peptide comprising the p16/matrix protein of human immunodeficiency virus type 2 (HIV-2$_{ROD}$), having the following sequence:

Met Gly Ala Arg Asn Ser Val Leu Arg Gly Lys

Lys Ala Asp Glu Leu Glu Arg Ile Arg Leu

Arg Pro Gly Gly Lys Lys Lys Tyr Arg Leu Lys

His Ile Val Trp Ala Ala Asn Lys Leu Asp

Arg Phe Gly Leu Ala Glu Ser Leu Leu Glu Ser

Leu Asp Pro Met Val Pro Thr Gly Ser Glu Asn

Leu Lys Ser Leu Phe Asn Thr Val Cys Val

Ile Trp Cys Ile His Ala Glu Glu Lys Val Lys

Asp Thr Glu Gly Ala Gln Ile Val Arg Arg

His Leu Val Ala Glu Thr Gly Thr Ala Glu Lys

Met Pro Ser Thr Ser Arg Pro Thr Ala Pro

Ser Ser Glu Lys Gly Gly Asn Tyr;

(11) a peptide comprising the p26/capsid protein of human immunodeficiency virus type 2 (HIV-$2_{ROD}$), having the following sequence:

Pro Val Gln His Val Gly Gly Asn Tyr Thr His

Ile Pro Leu Ser Pro Arg Thr Leu Asn Ala

Trp Val Lys Leu Val Glu Glu Lys Lys Phe Gly

Ala Glu Val Val Pro Gly Phe Gln Ala Leu

Ser Glu Gly Cys Thr Pro Tyr Asp Ile Asn Gln

Met Leu Asn Cys Val Gly Asp His Gln Ala

Ala Met Gln Ile Ile Arg Glu Ile Ile Asn Glu

Glu Ala Ala Glu Trp Asp Val Gln His Pro Ile

Pro Gly Pro Leu Pro Ala Gly Gln Leu Arg Glu

Pro Arg Gly Ser Asp Ile Ala Gly Thr Thr

Ser Thr Val Glu Glu Gln Ile Gln Trp Met Phe

Arg Pro Gln Asn Pro Val Pro Val Gly Asn

Ile Tyr Arg Arg Trp Ile Gln Ile Gly Leu Gln

Lys Cys Val Arg Met Tyr Asn Pro Thr Asn Ile

Leu Asp Ile Lys Gln Gly Pro Lys Glu Pro Phe

Gly Ser Tyr Val Asp Arg Phe Tyr Lys Ser

Leu Arg Ala Glu Gln Thr Asp Pro Ala Val Lys

Asn Trp Met Thr Gln Thr Leu Leu Val Gln

Asn Ala Asn Pro Asp Cys Lys Leu Val Leu Lys

Gly Leu Gly Met Asn Pro Thr Leu Glu Glu

Met Leu Thr Ala Cys Gln Gly Val Gly Gly Pro

Gly Gln Lys Ala Arg Leu Met Ala Glu Ala

-continued

Leu Lys Glu Val Ile Gly Pro Ala Pro Ile Pro

Phe Ala Ala Ala Gln Gln; and

(12) a peptide comprising the p12/nucleocapsid protein of human immunodeficiency virus type 2 (HIV-$2_{ROD}$), having the following sequence:

Arg Lys Ala Phe Lys Cys Trp Asn Cys Gly Lys

Glu Gly His Ser Ala Arg Gln Cys Arg Ala

Pro Arg Arg Gln Gly Cys Trp Lys Cys Gly Lys

Pro Gly His Ile Met Thr Asn Csy Pro Asp

Arg Gln Ala Gly Phe Leu Gly Leu Gly Pro Trp

Gly Lys Lys Pro Arg Asn Phe Pro Val Ala

Gln Val Pro Gln Gly Leu Thr Pro Thr Ala Pro

Pro Val Asp Pro Ala Val Asp Leu Leu Glu

Lys Tyr Met Gln Gln Gly Lys Arg Gln Arg Glu

Gln Arg Glu Arg Pro Tyr Lys Glu Val Thr

Glu Asp Leu Leu His Leu Glu Gln Gly Glu Thr

Pro Tyr Arg Glu Pro Pro Thr Glu Asp Leu

Leu His Leu Asn Ser Leu Phe Gly Lys Asp Gln;

(b) detecting the formation of antigen-antibody complex between said one or more peptides and antibodies present in said biological sample: and (c) providing a biological reference sample lacking antibodies recognized by said one or more peptides, wherein the one or more peptides and the biological reference sample are present in an amount sufficient to perform the detection of antigen-antibody complex formed between said one or more peptides and antibodies present in the biological sample, said detection being indicative of previous exposure to HIV-2.

10. The method of claim 9, wherein the formation of antigen-antibody complex is detected by employing a process selected from the group consisting of radioimmunoassay, radioimmunoprecipitation assay, immunofluorescence assay, enzyme-linked immunosorbent assay, and Western blot.

11. An in vitro diagnostic method for the detection of the presence or absence of antibodies which bind to antigens of a human immunodeficiency virus type 2 (HIV-2) comprising:

(a) contacting a biological sample with a peptide comprising the Nef protein of human immunodeficiency virus type 2 (HIV-$2_{ROD}$), having the following sequence:

Met Gly Ala Ser Gly Ser Lys Lys His Ser Arg Pro Pro Arg Gly Leu Gln Glu Arg Leu Leu

Arg Ala Arg Ala Gly Ala Cys Gly Gly Tyr Trp Asn Glu Ser Gly Gly Glu Tyr Ser Arg Phe

Gln Glu Gly Ser Asp Arg Glu Gln Lys Ser Pro Ser Cys Glu Gly Arg Gln Tyr Gln Gln Gly

Asp Phe Met Asn Thr Pro Trp Lys Asp Pro Ala Ala Glu Arg Glu Lys Asn Leu Try Arg Gln

Gln Asn Met Asp Asp Val Asp Ser Asp Asp Asp Asp Gln Val Arg Val Ser Val Thr Pro Lys

Val Pro Leu Arg Pro Met Thr His Arg Leu Ala Ile Asp Met Ser His Leu Ile Lys Thr Arg

-continued

Gly Gly Leu Glu Gly Met Phe Tyr Ser Glu Arg Arg His Lys Ile Leu Asn Ile Tyr Leu Glu

Lys Glu Glu Gly Ile Ile Ala Asp Trp Gln Asn Tyr Thr His Gly Pro Gly Val Arg Tyr Pro

Met Phe Phe Gly Trp Leu Trp Lys Leu Val Pro Val Asp Val Pro Gln Glu Gly Glu Asp Thr

Glu Thr His Cys Leu Val His Pro Ala Gln Thr Ser Lys Phe Asp Asp Pro His Gly Glu Thr

Leu Val Trp Glu Phe Asp Pro Leu Leu Ala Tyr Ser Tyr Glu Ala Phe Ile Arg Tyr Pro Glu

Glu Phe Gly His Lys Ser Gly Leu Pro Glu Glu Glu Trp Lys Ala Arg Leu Lys Ala Arg Gly

Ile Pro Phe Ser; and (b) detecting the formation of antigen-antibody complex between said peptide and antibodies present in said biological sample; and (c) providing a biological reference sample lacking antibodies recognized by said peptide.

wherein the peptide and the biological reference sample are present in an amount sufficient to perform the detection of antigen-antibody complex formed between said peptide and antibodies present in the biological sample, said detection being indicative of previous exposure to HIV-2.

12. The method of claim 11, wherein the formation of antigen-antibody complex is detected by employing a process selected from the group consisting of radioimmunoassay, radioimmunoprecipitation assay, immunofluorescence assay, enzyme-linked immunosorbent assay, and Western blot.

13. A diagnostic kit for the in vitro detection of the presence or absence of antibodies which bind to antigens of a human immunodeficiency virus type 2 (HIV-2) comprising:

(a) a peptide composition comprising one or more peptides selected from the group consisting of:

(1) a peptide comprising the gag precursor protein of human immunodeficiency virus type 2 (HIV-$2_{ROD}$), having the following sequence:

Met Gly Ala Arg Asn Ser Val Leu Arg Gly Lys Lys Ala Asp Glu Leu Glu Arg Ile Arg Leu

Arg Pro Gly Gly Lys Lys Lys Tyr Arg Leu Lys His Ile Val Trp Ala Ala Asn Lys Leu Asp

Arg Phe Gly Leu Ala Glu Ser Leu Leu Glu Ser Lys Glu Gly Cys Gln Lys Ile Leu Thr Val

Leu Asp Pro Met Val Pro Thr Gly Ser Glu Asn Leu Lys Ser Leu Phe Asn Thr Val Cys Val

Ile Trp Cys Ile His Ala Glu Glu Lys Val Lys Asp Thr Glu Gly Ala Lys Gln Ile Val Arg Arg

His Leu Val Ala Glu Thr Gly Thr Ala Glu Lys Met Pro Ser Thr Ser Arg Pro Thr Ala Pro

Ser Ser Glu Lys Gly Gly Asn Tyr Pro Val Gln His Val Gly Gly Asn Tyr Thr His Ile Pro

Leu Ser Pro Arg Thr Leu Asn Ala Trp Val Lys Leu Val Glu Glu Lys Lys Phe Gly Ala Glu

Val Val Pro Gly Phe Gln Ala Leu Ser Glu Gly Cys Thr Pro Tyr Asp Ile Asn Gln Met Leu

Asn Cys Val Gly Asp His Gln Ala Ala Met Gln Ile Ile Arg Glu Ile Ile Asn Glu Glu Ala Ala

Glu Trp Asp Val Gln His Pro Ile Pro Gly Pro Leu Pro Ala Gly Gln Leu Arg Glu Pro Arg

Gly Ser Asp Ile Ala Gly Thr Thr Ser Thr Val Glu Glu Gln Ile Gln Trp Met Phe Arg Pro Gln

Asn Pro Val Pro Val Gly Asn Ile Tyr Arg Arg Trp Ile Gln Ile Gly Leu Gln Lys Cys Val Arg

Met Tyr Asn Pro Thr Asn Ile Leu Asp Ile Lys Gln Gly Pro Lys Glu Pro Phe Gln Ser Tyr

Val Asp Arg Phe Tyr Lys Ser Leu Arg Ala Glu Gln Thr Asp Pro Ala Val Lys Asn Trp Met

Thr Gln Thr Leu Leu Val Gln Asn Ala Asn Pro Asp Cys Lys Leu Val Leu Lys Gly Leu Gly

Met Asn Pro Thr Leu Glu Glu Met Leu Thr Ala Cys Gln Gly Val Gly Gly Pro Gly Gln Lys

Ala Arg Leu Met Ala Glu Ala Leu Lys Glu Val Ile Gly Pro Ala Pro Ile Pro Phe Ala Ala Ala

Gln Gln Arg Lys Ala Phe Lys Cys Trp Asn Cys Gly Lys Glu Gly His Ser Ala Arg Gln Cys

Arg Ala Pro Arg Arg Gln Gly Cys Trp Lys Cys Gly Lys Pro Gly His Ile Met Thr Asn Cys

Pro Asp Arg Gln Ala Gly Phe Leu Gly Leu Gly Pro Trp Gly Lys Lys Pro Arg Asn Phe Pro

Val Ala Gln Val Pro Gln Gly Leu Thr Pro Thr Ala Pro Pro Val Asp Pro Ala Val Asp Leu

Leu Glu Lys Tyr Met Gln Gln Gly Lys Arg Gln Arg Glu Gln Arg Glu Arg Pro Tyr Lys Glu

Val Thr Glu Asp Leu Leu His Leu Glu Gln Gly Glu Thr Pro Tyr Arg Glu Pro Pro Thr Glu

Asp Leu Leu His Leu Asn Ser Leu Phe Gly Lys Asp Gln;

(2) a peptide comprising the polymerase precursor protein of human immunodeficiency virus type 2 (HIV-2$_{ROD}$), having the following sequence:

Thr Gly Arg Phe Phe Arg Thr Gly Pro Leu Gly Lys Glu Ala Pro Gln Leu Pro Arg Gly Pro

Ser Ser Ala Gly Ala Asp Thr Asn Ser Thr Pro Ser Gly Ser Ser Ser Gly Ser Thr Gly Glu Ile

Tyr Ala Ala Arg Glu Lys Thr Glu Arg Ala Glu Arg Glu Thr Ile Gln Gly Ser Asp Arg Gly

Leu Thr Aln Pro Arg Ala Gly Gly Asp Thr Ile Gln Gly Ala Thr Asn Arg Gly Leu Ala Ala

Pro Gln Phe Ser Leu Trp Lys Arg Pro Val Val Thr Ala Tyr Ile Glu Gly Gln Pro Val Glu Val

Leu Leu Asp Thr Gly Ala Asp Asp Ser Ile Val Ala Gly Ile Glu Leu Gly Asn Asn Tyr Ser

Pro Lys Ile Val Gly Gly Ile Gly Gly Phe Ile Asn Thr Lys Glu Tyr Lys Asn Val Glu Ile Glu

Val Leu Asn Lys Lys Val Arg Ala Thr Ile Met Thr Gly Asp Thr Pro Ile Asn Ile Phe Gly Arg

Asn Ile Leu Thr Ala Leu Gly Met Ser Leu Gly Met Ser Leu Asn Leu Pro Val Ala Lys Val

Glu Pro Ile Lys Ile Met Leu Lys Pro Gly Lys Asp Gly Pro Lys Leu Arg Gln Trp Pro Leu

Thr Lys Glu Lys Ile Glu Ala leu Lys Glu Ile Cys Glu Lys Met Glu Lys Glu Gly Gln Leu Glu Glu Ala Pro Pro Thr Asn Pro Tyr Asn Thr Pro Thr Phe Ala Ile Lys Lys Lys Asp Lys Asn Lys Trp Arg Met Leu Ile Asp Phe Arg Glu Leu Asn Lys Val Thr Gln Asp Phe Thr Glu Ile Gln Leu Gly Ile Pro His Pro Ala Gly Leu Ala Lys Lys Arg Arg Ile Thr Val Leu Asp Val Gly Asp Ala Tyr Phe Ser Ile Pro Leu His Glu Asp Phe Arg Pro Tyr Thr Ala Phe Thr Leu Pro Ser Val Asn Asn Ala Glu Pro Gly Lys Arg Tyr Ile Tyr Lys Val Leu Pro Gln Gly Trp Lys Gly Ser Pro Ala Ile Phe Gln His Thr Met Arg Gln Val leu Glu Pro Phe Arg Lys Ala Asn Lys Asp Val Ile Ile Ile Gln Tyr Met Asp Asp Ile Leu Ile Ala Ser Asp Arg Thr Asp Leu Glu His Asp Arg Val Val Leu Gln Leu Lys Glu Leu Leu Asn Gly leu Gly Phe Ser Thr Pro Asp Glu Lys Phe Gln Lys Asp Pro Pro Tyr His Trp Met Gly Tyr Glu Leu Trp Pro Thr Lys Trp Lys Leu Gln Lys Ile Gln Leu Pro Gln Lys Glu Ile Trp Thr Val Asn Asp Ile Gln Lys Leu Val Gly Val Leu Asn Trp Ala Ala Gln leu Tyr Pro Gly Ile Lys Thr Lys His Leu Cys Arg Leu Ile Arg Gly Lys Met Thr Leu Thr Glu Glu Val Gln Trp Thr Glu Leu Ala Glu Ala Glu Leu Glu Glu Asn Arg Ile Ile Leu Ser Gln Glu Gln Glu Gly His Tyr Tyr Gln Glu Glu Lys Glu Leu Glu Ala Thr Val Gln Lys Asp Gln Glu Asn Gln trp Thr Tyr Lys Ile His Gln Glu Glu Lys Ile Leu Lys Val Gly Lys Tyr Ala Lys Val Lys Asn Thr His Thr Asn Gly Ile Arg Leu Leu Ala Gln Val Val Gln Lys Ile Gly Lys Glu Ala Leu Val Ile Trp Gly Arg Ile Pro Lys Phe His Leu Pro Val Glu Arg Glu Ile Trp Glu Gln Trp Trp Asp Asn Tyr Trp Gln Val Thr Trp Ile Pro Asp Trp Asp Phe Val Ser Thr Pro Pro Leu Val Arg Leu Ala Phe Asn Leu Val Gly Asp Pro Ile Pro Gly Ala Glu Thr Phe Tyr Thr Asp Gly Ser Cys Asn Arg Gln Ser Lys Glu Gly Lys Ala Gly Tyr Val Thr Asp Arg Gly Lys Asp Lys Val Lys Lys Leu Glu Gln Thr Thr Asn Gln Gln Ala Glu Leu Glu Ala Phe Ala Met Ala Leu Thr Asp Ser Gly pro Lys Val Asn Ile Ile Val Asp Ser Gln Tyr Val Met Gly Ile Ser Ala Ser Gln Pro Thr Glu Ser Glu Ser Lys Ile Val Asn Gln Ile Ile Glu Glu Met Ile Lys Lys Glu Ala Ile Tyr Val Ala Trp Val Pro Ala His Lys Gly Ile Gly Gly Asn Gly Glu Val Asp His Leu Val Ser Gln Gly Ile Arg Gln Val Leu Phe Leu Glu Lys Ile Glu Pro Ala Gln Glu Glu His Glu Lys Tyr His Ser Asn Val Lys Glu Leu Ser His -continued

Lys Phe Gly Ile Pro Asn Leu Val Ala Arg Gln Ile Val Asn Ser Cys Ala Gln Cys Ala Gln Cys
Gln Gln Lys Gly Glu Ala Ile His Gly Gln Val Asn Ala Glu Leu Gly Thr Trp Gln Met Asp
Cys Thr His Leu Glu Gly Lys Ile Ile Ile Val Ala Val His Val Ala Ser Gly Phe Ile Glu Ala
Glu Val Ile Pro Gln Glu Ser Gly Arg Gln thr Ala Leu Phe Leu Leu Lys Leu Ala Ser Arg Trp
Pro Ile Thr His Leu His Thr Asp Asn Gly Ala Asn Phe Thr Ser Gln Glu Val Lys Met Val
Ala Trp Trp Ile Gly Ile Glu Gln Ser Phe Gly Val Pro Tyr Asn Pro Gln Ser Gln Gly Val Val
Glu Ala Met Asn His His Leu Lys Asn Gln Ile Ser Arg Ile Arg Glu Gln Ala asn Thr Ile Glu
Thr Ile Val Leu Met Ala Ile His Cys Met Asn Phe Lys Arg Arg Gly Gly Ile Gly Asp Met
Thr Pro Ser Glu Arg Leu Ile Asn Met Ile Thr Thr Glu Gln Glu Ile Gln Phe Leu Gln Ala Lys
Asn Ser Lys Leu Lys Asp Phe Arg Val Tyr Phe Arg Glu Gly Arg Asp Gln Leu Trp Lys Gly
Pro Gly Glu Leu Leu Trp Lys Gly Glu Gly Ala Val Leu Val Lys Val Gly Thr Asp Ile Lys
Ile Ile Pro Arg Arg Lys Ala Lys Ile Ile Arg Asp Tyr Gly Gly Arg Gln Glu Met Asp Ser Gly
Ser His Leu Glu Gly Ala Arg Glu Asp Gly Glu Met Ala;

(3) a peptide comprising the env precursor protein of
human immunodeficiency virus type 2 (HIV-2$_{ROD}$),
having the following sequence:

Met Met Asn Gln Leu Leu Ile Ala Ile Leu Leu Ala Ser Ala Cys Leu Val Tyr Cys Thr Gln
Tyr Val Thr Val Phe Tyr Gly Val Pro Thr Trp Lys Asn Ala Thr Thr Pro Leu Phe Cys Ala
Thr Arg Asn Arg Asp Thr Trp Gly Thr Ile Gln Cys Leu Pro Asp Asn Asp Asp Tyr Gln Glu
Ile Thr Leu Asn Val Thr Glu Ala Phe Asp Ala Trp Asn Asn Thr Val Thr Glu Gln Ala Ile
Glu Asp Val Trp His Leu Phe Glu Thr Ser Ile Lys Pro Cys Val Lys Leu Thr Pro Leu Cys
Val Ala Met Lys Cys Ser Ser Thr Glu Ser Ser Thr Gly Asn Asn Thr Thr Ser Lys Ser Thr Ser
Thr Thr Thr Thr Thr Pro Thr Asp Gln Glu Gln Glu Ile Ser Glu Asp Thr Pro Cys Ala Arg
Ala Asp Asn Cys Ser Gly Leu Gly Glu Glu Glu Thr Ile Asn Cys Gln Phe Asn Met Thr Gly
Leu Glu Arg Asp Lys Lys Lys Gln Tyr Asn Glu Thr Trp Tyr Ser Lys Asp Val Val Cys Glu
Thr Asn Asn Ser Thr Asn Gln Thr Gln Cys Tyr Met Asn His Cys Asn Thr Ser Val Ile Thr
Glu Ser Cys Asp Lys His Tyr Trp Asp Ala Ile Arg Phe Arg Tyr Cys Ala Pro Pro Gly Tyr
Ala Leu Leu Arg Cys Asn Asp Thr Asn Tyr Ser Gly Phe Ala Pro Asn Cys Ser Lys Val Val
Ala Ser Thr Cys Thr Arg Met Met Glu Thr Gln Thr Ser Thr Trp Phe Gly Phe Asn Gly Thr
Arg Ala Glu Asn Arg Thr Tyr Ile Tyr Trp His Gly Arg Asp Asn Arg Thr Ile Ile Ser Leu Asn
Lys Tyr Tyr Asn Leu Ser Leu His Cys Lys Arg Pro Gly Asn Lys Thr Val Lys Gln Ile Met
Leu Met Ser Gly His Val Phe His Ser His Tyr Gln Pro Ile Asn Lys Arg Pro Arg Gln Ala Trp
Cys Trp Phe Lys Gly Lys Trp Lys Asp Ala Met Gln Glu Val Lys Glu Thr Leu Ala Lys His
Pro Arg Tyr Arg Gly Thr Asn Asp Thr Arg Asn Ile Ser Phe Ala Ala Pro Gly Lys Gly Ser
Asp Pro Glu Val Ala Tyr Met Trp Thr Asn Cys Arg Gly Glu Phe Leu Tyr Cys Asn Met Thr
Trp Phe Leu Asn Trp Ile Glu Asn Lys Thr His Arg Asn Tyr Ala Pro Cys His Ile Lys Gln Ile
Ile Asn Thr Trp His Lys Val Gly Arg Asn Val Tyr Leu Pro Pro Arg Glu Gly Glu Leu Ser
Cys Asn Ser Thr Val Thr Ser Ile Ile Ala Asn Ile Asp Trp Gln Asn Asn Asn Gln thr Asn Ile
Thr Phe Ser Ala Glu Val Ala Glu Leu Tyr Arg Leu Glu Leu Gly Asp Tyr Lys Leu Val Glu
Ile Thr Pro Ile Gly Phe Ala Pro Thr Lys Glu Lys Arg Tyr Ser Ser Ala His Gly Arg His Thr
Arg Gly Val Phe Val Leu Gly Phe Leu Gly Phe Leu Ala Thr Ala Gly Ser Ala Met Gly Ala Ala Ser Leu Thr Val Ser Ala Gln Ser Arg Thr Leu Leu Ala Gly Ile Val Gln Gln Gln Gln Gln
Leu Leu Asp Val Val Lys Arg Gln Gln Glu Leu Leu Arg Leu Thr Val Trp Gly Thr Lys Asn
Leu Gln Ala Arg Val Thr Ala Ile Glu Lys Tyr Leu Gln Asp Gln Ala Arg Leu Asn Ser Trp
Gly Cys Ala Phe Arg Gln Val Cys His Thr Thr Val Pro Trp Val Asn Asp Ser Leu Ala Pro
Asp Trp Asp Asn Met Thr Trp Gln Glu Trp Glu Lys Gln Val Arg Tyr Leu Glu Ala Asn Ile
Ser Lys Ser Leu Glu Gln Ala Gln Ile Gln Gln Glu Lys Asn Met Tyr Glu Leu Gln Lys Leu
Asn Ser Trp Asp Ile Phe Gly Asn Trp Phe Asp Leu Thr Ser Trp Val Lys Tyr Ile Gln Tyr
Gly Val Leu Ile Ile Val Ala Val Ile Ala Leu Arg Ile Val Ile Tyr Val Val Gln Met Leu Ser
Arg Leu Arg Lys Gly Tyr Arg Pro Val Phe Ser Ser Pro Pro Gly Tyr Ile Gln Gln Ile His Ile
His Lys Asp Arg Gly Gln Pro Ala Asn Glu Glu Thr Glu Glu Asp Gly Gly Ser Asn Gly Gly
Asp Arg Tyr Trp Pro Trp Pro Ile Ala Tyr Ile His Phe Leu Ile Arg Gln Leu Ile Arg Leu Leu
Thr Arg Leu Tyr Ser Ile Cys Arg Asp Leu Leu Ser Arg Ser Phe Leu Thr Leu Gln Leu Ile
Tyr Gln Asn Leu Arg Asp Trp Leu Arg Leu Arg Thr Ala Phe Leu Gln Tyr Gly Cys Clu Trp
Ile Gln Glu Ala Phe Gln Ala Ala Ala Arg Ala Thr Arg Glu Thr Leu Ala Gly Ala Cys Arg
Gly Leu Trp Arg Val Leu Glu Arg Ile Gly Arg Gly Ile Leu Ala Val Pro Arg Arg Ile Arg
Gln Gly Ala Glu Ile Ala Leu Leu;

(4) a peptide comprising the Vif protein of human
immunodeficiency virus type 2 (HIV-2$_{ROD}$), having
the following sequence:

Met Glu Glu Asp Lys Arg Trp Ile Val Val Pro Thr Trp Arg Val Pro Gly Arg Met Glu Lys
Trp His Ser Leu Val Lys Tyr Leu Lys Tyr Lys Thr Lys Asp Leu Glu Lys Val Cys Tyr Val
Pro His His Lys Val Gly Trp Ala Trp Trp Thr Cys Ser Arg Val Ile Phe Pro Leu Lys Gly
Asn Ser his Leu Glu Ile Gln Ala Tyr Trp Asn Leu Thr Pro Glu Lys Gly Trp Leu Ser Ser
Tyr Ser Val Arg Ile Thr Trp Tyr Thr Glu Lys Phe Trp Thr Asp Val Thr Pro Asp Cys Ala
Asp Val Leu Ile His Ser Thr Tyr Phe Pro Cys Phe Thr Ala Gly Glu Val Arg Arg Ala Ile
Arg Gly Glu Lys Leu Leu Ser Cys Cys Asn Tyr Pro Arg Ala His Arg Ala Gln Val Pro Ser
Leu Gln Phe Leu Ala Leu Val Val Val Gln Gln Asn Asp Arg Pro Gln Arg Asp Ser Thr Thr
Arg Lys Gln Arg Arg Arg Asp Tyr Arg Arg Gly Leu Arg Leu Ala Lys Gln Asp Ser Arg Ser
His Lys Gln Arg Ser Ser Glu Ser Pro Thr Pro Arg Thr Tyr Phe Pro Gly Val Ala Glu Val
Leu Glu Ile Leu Ala;

(5) a peptide comprising the Vpr protein of human
immunodeficiency virus type 2 (HIV-2$_{ROD}$), having
the following sequence:

Met Ala Glu Ala Pro Thr Glu Leu Pro Pro Val Asp Gly Thr Pro Leu Arg Glu Pro Gly Asp
Glu Trp Ile Ile Glu Ile Leu Arg Glu Ile Lys Glu Glu Ala Leu Lys His Phe Asp Pro Arg Leu
Leu Ile Ala Leu Gly Lys Try Ile Tyr Thr Arg His Gly Asp Thr Leu Glu Gly Ala Arg Glu
Leu Ile Lys Val Leu Gln Arg Ala Leu Phe Thr His Phe Arg Ala Gly Cys Gly His Ser Arg
Ile Gly Gln Thr Arg Gly Gly Asn Pro Leu Ser Ala Ile Pro Thr Pro Arg Asn Met Gln;

(6) a peptide comprising the Vpx protein of human
immunodeficiency virus type 2 (HIV-2$_{ROD}$), having
the following sequence:

Met Thr Asp Pro Arg Glu Thr Val Pro Pro Gly Asn Ser Gly Glu Glu Thr Ile Gly Glu Ala
Phe Ala Trp Leu Asn Arg Thr Val Glu Ala Ile Asn Arg Glu Ala Val Asn His Leu Pro Arg
Glu Leu Ile Phe Gln Val Trp gln Arg Ser Trp Arg Tyr Trp His Asp Glu Gln Gly Met Ser
Glu Ser Tyr Thr Lys Tyr Arg Tyr Leu Cys Ile Ile Gln Lys Ala Val Tyr Met His Val Arg
Lys Gly Cys Thr Cys Leu Gly Arg Gly His Gly Pro Gly Gly Trp Arg Pro Gly Pro Pro Pro
Pro Pro Pro Pro Gly Leu Val;

(7) a peptide comprising the Nef protein of human immunodeficiency virus type 2 (HIV-2$_{ROD}$), having the following sequence:

Met Gly Ala Ser Gly Ser Lys Lys His Ser Arg Pro Pro Arg Gly Leu Gln Glu Arg Leu Leu
Arg Ala Arg Ala Gly Ala Cys Gly Gly Tyr Trp Asn Glu Ser Gly Gly Glu Tyr Ser Arg Phe
Gln Glu Gly Ser Asp Arg Glu Gln Lys Ser Pro Ser Cys Glu Gly Arg Gln Tyr Gln Gln Gly
Asp Phe Met Asn Thr Pro Trp Lys Asp Pro Ala Ala Glu Arg Glu Lys Asn Leu Try Arg Gln
Gln Asn Met Asp Asp Val Asp Ser Asp Asp Asp Gln Val Arg Val Ser Val Thr Pro Lys
Val Pro Leu Arg Pro Met Thr His Arg Leu Ala Ile Asp Met Ser His Leu Ile Lys Thr Arg
Gly Gly Leu Glu Gly Met Phe Tyr Ser Glu Arg Arg His Lys Ile Leu Asn Ile Tyr Leu Glu
Lys Glu Glu Gly Ile Ile Ala Asp Trp Gln Asn Tyr Thr His Gly Pro Gly Val Arg Tyr Pro
Met Phe Phe Gly Trp Leu Trp Lys Leu Val Pro Val Asp Val Pro Gln Glu Gly Glu Asp Thr
Glu Thr His Cys Leu Val His Pro Ala Gln Thr Ser Lys Phe Asp Asp Pro His Gly Glu Thr
Leu Val Trp Glu Phe Asp Pro Leu Leu Ala Tyr Ser Tyr Glu Ala Phe Ile Arg Tyr Pro Glu
Glu Phe Gly His Lys Ser Gly Leu Pro Glu Glu Glu Trp Lys Ala Arg Leu Lys Ala Arg Gly
Ile Pro Phe Ser;

(8) a peptide comprising the TAT protein of human immunodeficiency virus type 2 (HIV-2$_{ROD}$), having the following sequence:

Met Glu Thr Pro Leu Lys Ala Pro Glu Ser Ser Leu Lys Ser Cys Asn Glu Pro Phe Ser Arg
Thr Ser Glu Gln Asp Val Ala Thr Gln Glu Leu Ala Arg Gln Gly Glu Glu Ile Leu Ser Gln
Leu Tyr Arg Pro Leu Glu Thr Cys Asn Asn Ser Cys Tyr Cys Lys Arg Cys Cys Tyr His Cys
Gln Met Cys Phe Leu Asn Lys Gly Leu Gly Ile Cys Tyr Glu Arg Lys Gly Arg Arg Arg Arg
Thr Pro Lys Lys Thr Lys Thr His Pro Ser Pro Thr Pro Asp Lys Ser; and
Ile Ser Thr Arg Thr Gly Asp Ser Gln Pro Thr Lys Lys Gln Lys Lys Thr Val Glu Ala Thr
Val Glu Thr Asp Thr Gly Pro Gly Arg;

(9) a peptide comprising the Rev protein of human immunodeficiency virus type 2 (HIV-2$_{ROD}$), having the following sequence:

Met Asn Glu Arg Ala Asp Glu Glu Gly Leu Gln Arg Lys Leu Arg Leu Ile Arg Leu Leu His
Gln Thr; and
Asn Pro Tyr Pro Gln Gly Pro Gly Thr Ala Ser Gln Arg Arg Asn Arg Arg Arg Arg Trp Lys
Gln Arg Trp Arg Gln Ile Leu Ala Leu Ala Asp Ser Ile Tyr Thr Phe Pro Asp Pro Pro Ala
Asp Ser Pro Leu Asp Gln Thr Ile Gln His Leu Gln Gly Leu Thr Ile Gln Glu Leu Pro Asp
Pro Pro Thr His Leu Pro Glu Ser Gln Arg Leu Ala Glu Thr;

(10) a peptide comprising the p16/matrix protein of human immunodeficiency virus type 2 (HIV-2$_{ROD}$), having the following sequence:

Met Gly Ala Arg Asn Ser Val Leu Arg Gly Lys Lys Ala Asp Glu Leu Glu Arg Ile Arg Leu

Arg Pro Gly Gly Lys Lys Lys Tyr Arg Leu Lys His Ile Val Trp Ala Ala Asn Lys Leu Asp

Arg Phe Gly Leu Ala Glu Ser Leu Leu Glu Ser Lys Glu Gly Cys Gln Lys Ile Leu Thr Val

Leu Asp Pro Met Val Pro Thr Gly Ser Glu Asn Leu Lys Ser Leu Phe Asn Thr Val Cys Val

Ile Trp Cys Ile His Ala Glu Glu Lys Val Lys Asp Thr Glu Gly Ala Lys Gln Ile Val Arg Arg

His Leu Val Ala Glu Thr Gly Thr Ala Glu Lys Met Pro Ser Thr Ser Arg Pro Thr Ala Pro

Ser Ser Glu Lys Gly Gly Asn Tyr;

(11) a peptide comprising the p26/capsid protein of human immunodeficiency virus type 2 (HIV-2$_{ROD}$), having the following sequence:

Pro Val Gln His Val Gly Gly Asn Tyr Thr His Ile Pro Leu Ser Pro Arg Thr Leu Asn Ala

Trp Val Lys Leu Val Glu Glu Lys Lys Phe Gly Ala Glu Val Val Pro Gly Phe Gln Ala Leu

Ser Glu Gly Cys Thr Pro Tyr Asp Ile Asn Gln Met Leu Asn Cys Val Gly Asp His Gln Ala

Ala Met Gln Ile Ile Arg Glu Ile Ile Asn Glu Glu Ala Ala Glu Trp Asp Val Gln His Pro Ile

Pro Gly Pro Leu Pro Ala Gly Gln Leu Arg Glu Pro Arg Gly Ser Asp Ile Ala Gly Thr Thr

Ser Thr Val Glu Glu Gln Ile Gln Trp Met Phe Arg Pro Gln Asn Pro Val Pro Val Gly Asn

Ile Tyr Arg Arg Trp Ile Gln Ile Gly Leu Gln Lys Cys Val Arg Met Tyr Asn Pro Thr Asn Ile

Leu Asp Ile Lys Gln Gly Pro Lys Glu Pro Phe Gln Ser Tyr Val Asp Arg Phe Tyr Lys Ser

Leu Arg Ala Glu Gln Thr Asp Pro Ala Val Lys Asn Trp Met Thr Gln Thr Leu Leu Val Gln

Asn Ala Asn Pro Asp Cys Lys Leu Val Leu Lys Gly Leu Gly Met Asn Pro Thr Leu Glu Glu

Met Leu Thr Ala Cys Gln Gly Val Gly Gly Pro Gly Gln Lys Ala Arg Leu Met Ala Glu Ala

Leu Lys Glu Val Ile Gly Pro Ala Pro Ile Pro Phe Ala Ala Ala Gln Gln; and

(12) a peptide comprising the p12/nucleocapsid protein of human immunodeficiency virus type 2 (HIV-2$_{ROD}$), having the following sequence:

Arg Lys Ala Phe Lys Cys Trp Asn Cys Gly Lys Glu Gly His Ser Ala Arg Gln Cys Arg Ala

Pro Arg Arg Gln Gly Cys Trp Lys Cys Gly Lys Pro Gly His Ile Met Thr Asn Cys Pro Asp
Arg Gln Ala Gly Phe Leu Gly Leu Gly Pro Trp Gly Lys Lys Pro Arg Asn Phe Pro Val Ala
Gln Val Pro Gln Gly Leu Thr Pro Thr Ala Pro Pro Val Asp Pro Ala Val Asp Leu Leu Glu
Lys Tyr Met Gln Gln Gly Lys Arg Gln Arg Glu Gln Arg Glu Arg Pro Tyr Lys Glu Val Thr
Glu Asp Leu Leu His Leu Glu Gln Gly Glu Thr Pro Tyr Arg Glu Pro Pro Thr Glu Asp Leu
Leu His Leu Asn Ser Leu Phe Gly Lys Asp Gln;

(b) reagents for the detection of the formation of antigen-antibody complex; and (c) a biological reference sample lacking antibodies recognized by said peptide composition, wherein the peptide composition, reagents, and biological reference sample are present in an amount sufficient to perform the detection of antigen-antibody complex formed between said one or more peptides and antibodies present in the biological sample, said detection being indicative of previous exposure to HIV-2.

14. A diagnostic kit for the in vitro detection of the presence or absence of antibodies which bind to antigens of a human immunodeficiency virus type 2 (HIV-2) comprising:

(a) a peptide having the following sequence:

Met Gly Ala Ser Gly Ser Lys Lys His Ser Arg Pro Pro Arg Gly Leu Gln Glu Arg Leu Leu
Arg Ala Arg Ala Gly Ala Cys Gly Gly Tyr Trp Asn Glu Ser Gly Gly Glu Tyr Ser Arg Phe
Gln Glu Gly Ser Asp Arg Glu Gln Lys Ser Pro Ser Cys Glu Gly Arg Gln Tyr Gln Gln Gly
Asp Phe Met Asn Thr Pro Trp Lys Asp Pro Ala Ala Glu Arg Glu Lys Asn Leu Try Arg Gln
Gln Asn Met Asp Asp Val Asp Ser Asp Asp Asp Gln Val Arg Val Ser Val Thr Pro Lys
Val Pro Leu Arg Pro Met Thr His